(12) United States Patent
Wells et al.

(10) Patent No.: US 12,144,506 B2
(45) Date of Patent: *Nov. 19, 2024

(54) METHODS FOR ANEURYSM TREATMENT

(71) Applicant: Nectero Medical, Inc., Tempe, AZ (US)

(72) Inventors: Eric Wells, Mesa, AZ (US); Kelvin Ning, Scottsdale, AZ (US)

(73) Assignee: Nectero Medical, Inc, Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/190,692

(22) Filed: Mar. 27, 2023

(65) Prior Publication Data

US 2023/0233209 A1 Jul. 27, 2023

Related U.S. Application Data

(63) Continuation of application No. 17/131,447, filed on Dec. 22, 2020, which is a continuation of application No. PCT/US2019/024140, filed on Mar. 26, 2019.
(Continued)

(51) Int. Cl.
    *A61B 17/12* (2006.01)
    *A61K 31/7032* (2006.01)
    (Continued)

(52) U.S. Cl.
    CPC .. *A61B 17/12113* (2013.01); *A61B 17/12136* (2013.01); *A61K 31/7032* (2013.01);
    (Continued)

(58) Field of Classification Search
    CPC ...... A61M 25/1011; A61M 2025/1086; A61M 2025/105; A61M 2025/1052;
    (Continued)

(56) References Cited

U.S. PATENT DOCUMENTS

| | | |
|---|---|---|
| 4,404,971 A | 9/1983 | LeVeen et al. |
| 4,423,725 A | 1/1984 | Baran et al. |
| | (Continued) | |

FOREIGN PATENT DOCUMENTS

| | | |
|---|---|---|
| CN | 200951251 | 9/2007 |
| CN | 101480407 | 7/2009 |
| | (Continued) | |

OTHER PUBLICATIONS

Allen et al. [Eds.], Ansel's Introduction to Pharmaceutical Dosage Forms and Drug Delivery Systems; 8th Edition (2004); Book Cover.
(Continued)

*Primary Examiner* — Shefali D Patel
*Assistant Examiner* — William R Frehe
(74) *Attorney, Agent, or Firm* — Knobbe Martens Olson & Bear LLP

(57) ABSTRACT

Disclosed herein is a method of producing high purity pentagalloyl glucose (PGG), analogues or derivatives thereof, at least 99.9% pure, by washing with dimethyl ether. The PGG may be provided in a kit, including a hydrolyzer for dissolving the PGG and a saline solution. Also disclosed herein is a device for delivery of a therapeutic solution to a blood vessel. The device may be a catheter having an upstream balloon and a downstream balloon. The upstream balloon may be expanded to anchor the catheter and occlude antegrade blood flow. The downstream balloon may be expanded to occlude retrograde blood flow, creating a sealed volume within the blood vessel. The downstream balloon may have pores configured to deliver the therapeutic solution into the sealed volume or a portion of the sealed volume The downstream balloon may be expanded by an expansion of a balloon disposed inside the downstream balloon.

20 Claims, 10 Drawing Sheets

Related U.S. Application Data

(60) Provisional application No. 62/714,346, filed on Aug. 3, 2018.

(51) Int. Cl.

| | |
|---|---|
| *A61K 47/10* | (2017.01) |
| *A61K 47/20* | (2006.01) |
| *A61L 29/16* | (2006.01) |
| *A61M 25/10* | (2013.01) |
| *C07H 1/06* | (2006.01) |
| *C07H 13/06* | (2006.01) |
| *C07H 13/08* | (2006.01) |

(52) U.S. Cl.
CPC .............. *A61K 47/10* (2013.01); *A61K 47/20* (2013.01); *A61L 29/16* (2013.01); *A61M 25/1011* (2013.01); *C07H 1/06* (2013.01); *C07H 13/08* (2013.01); *A61L 2300/232* (2013.01); *A61M 2025/105* (2013.01); *A61M 2025/1052* (2013.01); *A61M 2025/1086* (2013.01); *A61M 2205/0238* (2013.01)

(58) Field of Classification Search
CPC .............. A61M 25/1006; A61M 25/10; A61M 25/1002; A61M 25/1018; A61M 25/10184; A61M 2025/1043; A61M 2202/0486; A61M 2205/3331; A61M 2210/12; A61B 17/12113; A61B 17/12031; A61B 17/12045; A61B 17/12109; A61B 17/12136; A61B 17/12186; A61B 17/12022; A61B 17/12027; A61B 2017/12127

See application file for complete search history.

(56) References Cited

U.S. PATENT DOCUMENTS

| | | | |
|---|---|---|---|
| 4,577,631 A * | 3/1986 | Kreamer | A61F 2/07 |
| | | | 606/198 |
| 4,741,915 A | 5/1988 | Farr | |
| 5,041,090 A | 8/1991 | Scheglov et al. | |
| 5,405,322 A | 4/1995 | Lennox et al. | |
| 5,489,295 A | 2/1996 | Piplani et al. | |
| 5,611,775 A | 3/1997 | Machold et al. | |
| 5,857,998 A | 1/1999 | Barry | |
| 5,868,776 A | 2/1999 | Wright | |
| 5,919,163 A | 7/1999 | Glickman | |
| 6,048,332 A | 4/2000 | Duffy et al. | |
| 6,575,932 B1 | 6/2003 | O'Brien et al. | |
| 6,706,013 B1 | 3/2004 | Bhat et al. | |
| 7,252,834 B2 | 8/2007 | Vyavahare | |
| 7,314,484 B2 | 1/2008 | Deem et al. | |
| 7,323,169 B2 | 1/2008 | Goldenberg | |
| 7,713,543 B2 | 5/2010 | Vyavahare | |
| 7,732,399 B2 | 6/2010 | Goldenberg | |
| 7,772,381 B2 | 8/2010 | Himmeldirk | |
| 8,034,022 B2 | 10/2011 | Boatman | |
| 8,100,961 B2 | 1/2012 | Vyavahare | |
| 8,142,805 B1 | 3/2012 | Vyavahare | |
| 8,317,747 B2 | 11/2012 | Kusleika | |
| 8,357,796 B2 | 1/2013 | Ren et al. | |
| 8,435,553 B2 | 5/2013 | Vyavahare | |
| 8,444,624 B2 | 5/2013 | Ogle et al. | |
| 8,496,911 B2 | 7/2013 | Weldon et al. | |
| 8,591,461 B2 | 11/2013 | Boatman | |
| 8,642,578 B2 | 2/2014 | Mitts | |
| 8,827,953 B2 | 9/2014 | Rochal-Singh | |
| 8,911,468 B2 | 12/2014 | Ogle et al. | |
| 9,044,570 B2 | 6/2015 | Weldon | |
| 9,181,290 B2 | 11/2015 | Liu et al. | |
| 9,277,923 B2 | 3/2016 | Rangi | |
| 9,283,241 B2 | 3/2016 | Simonescu | |
| 9,370,644 B2 | 6/2016 | Rochal-Singh | |
| 9,795,573 B2 | 10/2017 | Vyavahare | |
| 9,889,279 B2 | 2/2018 | Ogle et al. | |
| 9,907,818 B2 | 3/2018 | Huang et al. | |
| 9,937,255 B2 | 4/2018 | Ogle et al. | |
| 11,007,351 B2 | 5/2021 | Bacino et al. | |
| 11,331,102 B2 * | 5/2022 | Wells | A61B 17/12113 |
| 2001/0016724 A1 | 8/2001 | Davis et al. | |
| 2001/0041862 A1 | 11/2001 | Glickman | |
| 2002/0115982 A1 | 8/2002 | Barbut et al. | |
| 2003/0036728 A1 | 2/2003 | Samson et al. | |
| 2004/0153025 A1 | 8/2004 | Seifert et al. | |
| 2004/0153120 A1 | 8/2004 | Seifert et al. | |
| 2004/0153145 A1 | 8/2004 | Simonescu | |
| 2005/0027247 A1 | 2/2005 | Carrison et al. | |
| 2005/0085685 A1 | 4/2005 | Barbut | |
| 2005/0158272 A1 | 7/2005 | Whirley | |
| 2006/0079923 A1 | 4/2006 | Chhabra et al. | |
| 2007/0150041 A1 | 6/2007 | Evans et al. | |
| 2007/0259030 A1 | 11/2007 | Drapeau | |
| 2007/0281026 A1 | 12/2007 | Vyavahare et al. | |
| 2007/0282422 A1 | 12/2007 | Biggs et al. | |
| 2007/0293937 A1 | 12/2007 | Biggs et al. | |
| 2008/0208163 A1 | 8/2008 | Wilkie | |
| 2008/0249299 A1 | 10/2008 | Ren et al. | |
| 2009/0155337 A1 | 6/2009 | Schreck | |
| 2009/0186370 A1 | 7/2009 | Ogle et al. | |
| 2009/0198266 A1 | 8/2009 | Cesare | |
| 2009/0203150 A1 | 8/2009 | Chen | |
| 2009/0214654 A1 * | 8/2009 | Isenburg | A61K 9/06 |
| | | | 514/25 |
| 2009/0254064 A1 | 10/2009 | Boatman | |
| 2009/0270964 A1 | 10/2009 | Huetter et al. | |
| 2010/0016833 A1 | 1/2010 | Ogle | |
| 2010/0119605 A1 | 5/2010 | Isenburg | |
| 2010/0261662 A1 | 10/2010 | Schreck | |
| 2011/0081423 A1 | 4/2011 | Weldon et al. | |
| 2011/0093000 A1 | 4/2011 | Ogle et al. | |
| 2011/0104233 A1 | 5/2011 | Drapeau | |
| 2011/0125132 A1 | 5/2011 | Krolik et al. | |
| 2011/0218517 A1 | 9/2011 | Ogle et al. | |
| 2012/0015019 A1 | 1/2012 | Pacetti et al. | |
| 2012/0143054 A1 | 6/2012 | Eaton et al. | |
| 2012/0184982 A1 | 7/2012 | Herbowy et al. | |
| 2012/0316436 A1 | 12/2012 | Lentz et al. | |
| 2012/0321566 A1 | 12/2012 | Liu et al. | |
| 2012/0323211 A1 * | 12/2012 | Ogle | A61L 29/145 |
| | | | 604/500 |
| 2014/0017263 A1 | 1/2014 | Vyavahare | |
| 2014/0039459 A1 | 2/2014 | Folk et al. | |
| 2014/0200504 A1 | 7/2014 | Rocha-Singh | |
| 2014/0243873 A1 * | 8/2014 | Franklin | A61B 17/12136 |
| | | | 606/194 |
| 2015/0005744 A1 | 1/2015 | Ogle et al. | |
| 2015/0087611 A1 | 3/2015 | Vyavahare et al. | |
| 2015/0190619 A1 | 7/2015 | Rocha-Singh | |
| 2016/0082178 A1 * | 3/2016 | Agah | A61B 6/504 |
| | | | 600/435 |
| 2016/0136109 A1 | 5/2016 | Isenburg et al. | |
| 2016/0339212 A1 * | 11/2016 | Bacino | A61L 29/041 |
| 2016/0348068 A1 | 12/2016 | Hagay et al. | |
| 2017/0007584 A1 | 1/2017 | Yeritsyan | |
| 2017/0209592 A1 | 7/2017 | Vyavahare et al. | |
| 2017/0258613 A1 | 9/2017 | Franano et al. | |
| 2017/0281140 A1 | 10/2017 | Arahira et al. | |
| 2017/0340434 A1 | 11/2017 | Cerchiari et al. | |
| 2017/0354523 A1 | 12/2017 | Chou et al. | |
| 2018/0036261 A1 | 2/2018 | Vyavahare et al. | |
| 2018/0064565 A1 | 3/2018 | MacTaggart et al. | |
| 2018/0214469 A1 | 8/2018 | Chen et al. | |
| 2018/0326071 A1 | 11/2018 | Ogle et al. | |
| 2018/0338766 A1 | 11/2018 | Ogle et al. | |
| 2018/0344665 A1 | 12/2018 | Isenburg et al. | |
| 2018/0344990 A1 | 12/2018 | Ogle et al. | |
| 2019/0070026 A1 * | 3/2019 | Fulton | A61K 38/1761 |
| 2019/0117242 A1 * | 4/2019 | Lawinger | A61B 18/26 |
| 2021/0106339 A1 | 4/2021 | Wells et al. | |
| 2021/0147462 A1 | 5/2021 | Wells et al. | |
| 2021/0308433 A1 | 10/2021 | Gifford, III et al. | |

(56) References Cited

U.S. PATENT DOCUMENTS

| | | |
|---|---|---|
| 2022/0000896 A1 | 1/2022 | Ning |
| 2022/0000897 A1 | 1/2022 | Ning |
| 2023/0233210 A1 | 7/2023 | Murphy |
| 2023/0310475 A1 | 10/2023 | Ning |

FOREIGN PATENT DOCUMENTS

| | | |
|---|---|---|
| CN | 101525357 | 9/2009 |
| CN | 101926394 | 12/2010 |
| CN | 102698354 | 10/2012 |
| CN | 102887924 | 1/2013 |
| CN | 203852722 U | 10/2014 |
| CN | 106699819 | 5/2017 |
| CN | 106905480 | 6/2017 |
| CN | 107550534 A | 1/2018 |
| DE | 103 02 241 | 8/2004 |
| EP | 2508221 A1 | 10/2012 |
| JP | 2008007468 | 1/2008 |
| JP | 2017176385 | 10/2017 |
| WO | WO 1987/005297 | 9/1987 |
| WO | WO 1998/009670 | 3/1998 |
| WO | WO 2000/018416 | 4/2000 |
| WO | WO 2001/070325 A2 | 9/2001 |
| WO | WO 2008/123937 A1 | 10/2008 |
| WO | WO 2009/105265 A2 | 8/2009 |
| WO | WO 2010/008513 | 1/2010 |
| WO | WO 2012/158944 | 11/2012 |
| WO | WO 2016/044647 | 3/2016 |
| WO | WO 2016/079330 | 5/2016 |
| WO | WO 2020/027882 | 2/2020 |

OTHER PUBLICATIONS

Banker et al., [Eds.] Modern Pharmaceutics, 4th Ed., Chapters 9 and 10 (2002) in 98 pages.

Chen et al., "Preparation of 1,2,3,4,6-penta-O-galloyl-[U-14C]-D-glucopyranose". J Label Comp Radiopharma. Jan. 2003;46(1): 99-105. (published online Nov. 21, 2002).

Chen et al., "Characterization of soluble non-covalent complexes between bovine serum albumin and beta-1,2,3,4,6-penta-O-galloyl-D-glucopyranose by MALDI-TOF MS", J Agricult Food Chem. Jun. 16, 2004; 52(12): 4008-4011.

Gilman et al. (Eds.) Goodman and Gilman's: The Pharmacological Basis of Therapeutics, 8th Ed., Pergamon Press (1990) TOC in 8 pages.

Institute of International Medical Education [IIME], "Glossary of Medical Education Terms"; http://www.iime.org/glossary.htm; accessed in Mar. 2013, 22 pages.

Isenburg et al., "Elastin Stabilization for Treatment of Abdominal Aortic Aneurysms". Circulation Apr. 3, 2007; 115(3): 1729-1737.

Kloster et al., "Inhibition of Early AAA Formation by Aortic Intraluminal Pentagalloyl Glucose (PGG) Infusion in a Novel Porcine AAA Model". Ann Med Surg. May 1, 2016;7: 65-70.

Li et al., "Preparation of penta-O-galloyl-βb-d-glucose from tannic acid and plasma pharmacokinetic analyses by liquid-liquid extraction and reverse-phase HPLC", J Pharma Biomed Anal. Feb. 20, 2011; 54(3): 545-550.

Lieberman et al. [Eds.], Pharmaceutical Dosage Forms: Tablets (1989); TOC in 7 pages.

Nema et al., "Excipients and Their Role in Approved Injectable Products: Current Usage and Future Directions". PDA J Pharm Sci and Tech. May 1, 2011;65(3): 287-332.

Nosoudi et al., "Reversal of Vascular Calcification and Aneurysms in a Rat Model Using Dual Targeted Therapy with EDTA- and PGG-loaded Nanoparticles". Theranostics. 2016;6(11): 1975-1987.

Powell et al., "Compendium of Excipients for Parenteral Formulations". PDA J Pharm Sci and Tech. Sep. 1, 1998;52(5): 238-311.

Remington's The Science and Practice of Pharmacy, 21st Ed., Lippincott Williams & Wilkins (2005), TOC in 4 pages.

Shaffer, C. Dr., "What is Elastin?", News Medical (online); 2019; downloaded from URL https://www.news-medical.net/life-sciences/What-is-Elastin.aspx; on Apr. 22, 2022; 4 pages. (year 2019).

Torres-León et al., "Pentagalloylglucose (PGG): A Valuable Phenolic Compound with Functional Properties". J Funct Foods, Oct. 1, 2017;37: 176-189.

Zhang et al., "Anti-cancer, Anti-diabetic and Other Pharmacologic and Biological Activities of Penta-galloyl-glucose". Pharm Res., Sep. 2009;26(9): 2066-2080.

Zhao et al., "Research Progress of Hydrolyzed Tannin PGG as a Traditional Chinese Medicine". J Clin Exp Med. Mar. 2013;12(6): 462-464.

International Search Report and Written Opinion; Int'l Application No. PCT/US2019/24142; dated Jul. 19, 2019.

International Search Report and Written Opinion; Int'l Application No. PCT/US19/24140; dated Jun. 21, 2019.

Extended European Search Report dated Apr. 4, 2022 for Application No. 19845328.4 in 8 pages.

Extended European Search Report dated May 30, 2022 for Application No. 19844863.1 in 12 pages.

Ahldén et al., "Knee laxity measurements after anterior cruciate ligament reconstruction, using either bone-patellar-tendon-bone or hamstring tendon autografts, with special emphasis on comparison over time." Knee Surg Sports Traumatol Arthrosc. Sep. 2009;17(9): 1117-1124.

* cited by examiner

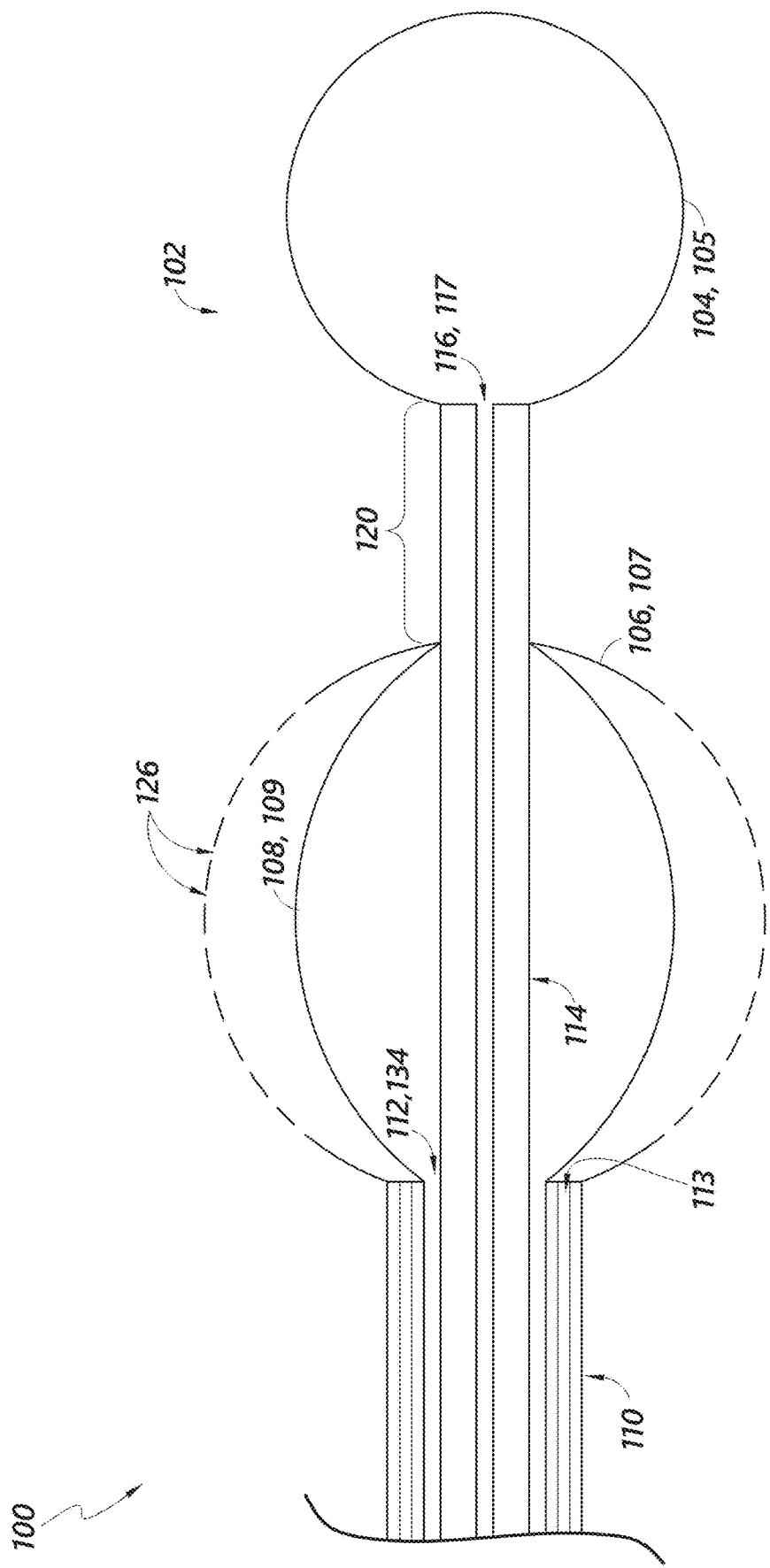

METHODS FOR ANEURYSM TREATMENT

RELATED APPLICATIONS

This application is a continuation of U.S. patent application Ser. No. 17/131,447 filed Dec. 22, 2020, which is a continuation of PCT/US2019/024140 filed Mar. 26, 2019, which claims the priority benefit of U.S. Provisional Application No. 62/714,346 filed Aug. 3, 2018, the entire content of each of which is hereby incorporated by reference herein in its entirety.

BACKGROUND

One of the most common results of the degradation of vasculature is aneurysm. By definition, the term "aneurysm" is simply an abnormal widening or ballooning at the wall of a blood vessel. Aneurysms are degenerative diseases characterized by destruction of arterial architecture and subsequent dilatation of the blood vessel that may eventually lead to fatal ruptures. Some common locations for aneurysms include the abdominal aorta (abdominal aortic aneurysm, AAA), thoracic aorta, and brain arteries. In addition, peripheral aneurysms of the leg, namely the iliac, popliteal and femoral arteries are prevalent locations of this vascular pathology. The occurrence of such peripheral aneurysms appears to be strongly associated with the presence of aneurysms in other locations, as it has been estimated that 30 to 60% of peripheral aneurysm patients also have an AAA.

Aneurysms can be devastating due to the potential for rupture or dissection that can lead to massive bleeding, stroke, or hemorrhagic shock, and can be fatal in an estimated 80% of cases. Aneurysms can be caused by any of a large class of degenerative diseases and pathologies including atherosclerotic disease, defects in arterial components, genetic susceptibilities, and high blood pressure, among others, and can develop silently over a period of years. The hallmarks of aneurysms include enzymatic degradation of vascular structural proteins such as elastin, collagen, inflammatory infiltrates, calcification, and eventual overall destruction of the vascular architecture. Elastin content in an aneurysmal aorta can be greatly reduced (for example, 70% less) than that of a healthy, undamaged aorta.

Aneurysms grow over a period of years and pose great risks to health. Aneurysms have the potential to dissect or rupture, causing massive bleeding, stroke, and hemorrhagic shock, which can be fatal in more than 80% of cases. AAAs are a serious health concern, specifically for the aging population, being among the top ten causes of death for patients older than 50. The estimated incidence for abdominal aortic aneurysm is about 50 in every 100,000 persons per year. Approximately 50,000 operations are performed each year in the U.S. for AAAs alone. In children, AAAs can result from blunt abdominal injury or from Marfan's syndrome, a defect in elastic fiber formation in walls of major arteries, such as the aorta.

Current methods of treatment for diagnosed aneurysms are limited to invasive surgical techniques. After initial diagnosis of a small aneurysm, the most common medical approach is to follow up the development of the aneurysm and after reaching a pre-determined size (for example, about 5 cm in diameter), surgical treatment is applied. Current surgical treatments are limited to either an endovascular stent graft repair or optionally complete replacement of the diseased vessel with a vascular graft. While such surgical treatments can save lives and improve quality of life for those suffering aneurysms, dangers beyond those of the surgery itself still exist for the patient due to possible post-surgery complications (for example, neurological injuries, bleeding, or stroke) as well as device-related complications (for example, thrombosis, leakage, or failure). Moreover, depending upon the location of the aneurysm, the danger of an invasive surgical procedure may outweigh the possible benefits of the procedure, for instance in the case of an aneurysm deep in the brain, leaving the sufferer with very little in the way of treatment options. Moreover, surgical treatments may not always provide a permanent solution, as vascular grafts can loosen and dislodge should the aneurysm progress following the corrective surgery. For some patients, the particular nature of the aneurysm or the condition of the patient makes the patient unsuitable for graft repair.

Aneurysm is not the only condition for which enzymatic degradation of structural proteins is a hallmark. Other conditions in which structural protein degradation appears to play a key role include Marfan syndrome, supravalvular aortic stenosis. For those afflicted, such conditions lead to, at the very least, a lowered quality of life and often, premature death.

Phenolic compounds are a diverse group of materials that have been recognized for use in a wide variety of applications. For instance, they naturally occur in many plants, and are often a component of the human diet. Phenolic compounds have been examined in depth for efficacy as free radical scavengers and neutralizers, for instance in topical skin applications and in food supplements. Phenolic compounds are also believed to prevent cross-linking of cell membranes found in certain inflammatory conditions and are believed to affect the expressions of specific genes due to their modulation of free radicals and other oxidative species (see, for example, U.S. Pat. No. 6,437,004 to Perricone).

What is needed in the art are treatment protocols and compositions for stabilization of the organs and tissues affected by degenerative conditions such as aneurysm. In particular, treatment protocols utilizing phenolic compounds could provide a safe, less invasive route for the stabilization of the structural architecture in order to temper growth and/or development of such conditions.

SUMMARY

Some embodiments provide a composition comprising a compound of the following Formula:

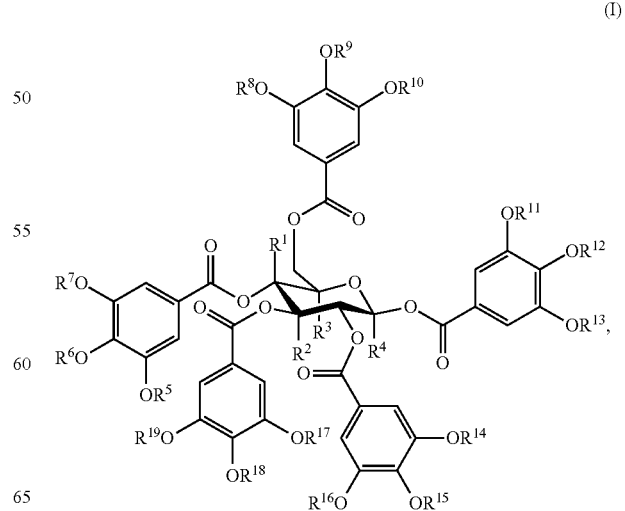

or a pharmaceutically acceptable salt thereof, wherein: $R^1$-$R^{19}$ have any of the values described herein, and wherein the composition is substantially free of gallic acid or methyl gallate. In some embodiments, substantially free is less than about 0.5% gallic acid. In some embodiments, substantially free is less than about 0.5% methyl gallate.

In some embodiments, $R^1$, $R^2$, $R^3$ and $R^4$ are each independently hydrogen or $R^A$;

$R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ are each independently hydrogen or $R^B$;

each $R^A$ is independently selected from the group consisting of —$OR^X$, —$N(R^Y)_2$, halo, cyano, —$C(=X)R^Z$, —$C(=X)N(R^Y)_2$, —$C(=X)OR^X$, —$OC(=X)R^Z$, —$OC(=X)N(R^Y)_2$, —$OC(=X)OR^X$, —$NR^YC(=X)R^Z$, —$NR^YC(=X)N(R^Y)_2$, —$NR^YC(=X)OR^X$, unsubstituted $C_{1-12}$alkoxy, substituted $C_{1-12}$alkoxy, unsubstituted $C_{1-8}$alkyl, substituted $C_{1-8}$alkyl, unsubstituted $C_{6\ or\ 10}$aryl, substituted $C_{6\ or\ 10}$aryl, unsubstituted $C_{7-12}$aralkyl, substituted $C_{7-12}$aralkyl, unsubstituted 5-10 membered heteroaryl, substituted 5-10 membered heteroaryl, unsubstituted $C_{3-12}$ heteroaralkyl, substituted $C_{3-12}$heteroaralkyl, unsubstituted 3-10 membered heterocyclyl, and substituted 3-10 membered heterocyclyl;

each $R^B$ is independently selected from the group consisting of —$C(=X)R^Z$, —$C(=X)N(R^Y)_2$, —$C(=X)OR^X$, unsubstituted $C_{1-8}$alkyl, substituted $C_{1-8}$alkyl, unsubstituted $C_{6\ or\ 10}$aryl, substituted $C_{6\ or\ 10}$aryl, unsubstituted $C_{7-12}$aralkyl, substituted $C_{7-12}$aralkyl, unsubstituted 5-10 membered heteroaryl, substituted 5-10 membered heteroaryl, unsubstituted 3-10 membered heterocyclyl and substituted 3-10 membered heterocyclyl, or two adjacent $R^B$ groups together with the atoms to which they are attached form an unsubstituted 3-10 heterocyclyl, a substituted 3-10 heterocyclyl, unsubstituted 5-10 membered heteroaryl ring or substituted 5-10 membered heteroaryl ring;

each X is independently oxygen (O) or sulfur (S);

each $R^X$ and $R^Y$ is independently selected from the group consisting of hydrogen, unsubstituted $C_{1-8}$alkyl, substituted $C_{1-8}$alkyl, unsubstituted $C_{6\ or\ 10}$aryl, substituted $C_{6\ or\ 10}$aryl, unsubstituted $C_{7-12}$aralkyl, substituted $C_{7-12}$aralkyl, unsubstituted 5-10 membered heteroaryl, substituted 5-10 membered heteroaryl, unsubstituted 3-10 membered heterocyclyl and substituted 3-10 membered heterocyclyl; and each $R^Z$ is independently selected from the group consisting of unsubstituted $C_{1-12}$alkoxy, substituted $C_{1-12}$alkoxy, unsubstituted $C_{1-8}$alkyl, substituted $C_{1-8}$alkyl, unsubstituted $C_{6\ or\ 10}$aryl, substituted $C_{6\ or\ 10}$aryl, unsubstituted $C_{7-12}$aralkyl, substituted $C_{7-12}$aralkyl, unsubstituted 5-10 membered heteroaryl, substituted 5-10 membered heteroaryl, unsubstituted 3-10 membered heterocyclyl and substituted 3-10 membered heterocyclyl.

In some embodiments, at least one of $R^1$, $R^2$, $R^3$ and $R^4$ is $R^A$. In some embodiments, at least two of $R^1$, $R^2$, $R^3$ and $R^4$ are $R^A$. In some embodiments, each $R^A$ is independently selected from the group consisting of —$OR^X$, —$N(R)_2$, halo, cyano, —$C(=X)R^Z$, —$C(=X)N(R)_2$, —$C(=X)OR^X$, —$OC(=X)R^Z$, —$OC(=X)N(R)_2$, —$OC(=X)OR^X$, —$NR^YC(=X)R^Z$, —$NR^YC(=X)N(R^Y)_2$, and —$NR^YC(=X)OR^X$. In some embodiments, each $R^A$ is independently selected from the group consisting of unsubstituted $C_{1-12}$alkoxy, substituted $C_{1-12}$alkoxy, unsubstituted $C_{1-8}$alkyl, substituted $C_{1-8}$alkyl, unsubstituted $C_{6\ or\ 10}$aryl, substituted $C_{6\ or\ 10}$aryl, unsubstituted $C_{7-12}$aralkyl, substituted $C_{7-12}$aralkyl, unsubstituted 5-10 membered heteroaryl, substituted 5-10 membered heteroaryl, unsubstituted $C_{3-12}$ heteroaralkyl, substituted $C_{3-12}$heteroaralkyl, unsubstituted 3-10 membered heterocyclyl, and substituted 3-10 membered heterocyclyl. In some embodiments, each $R^A$ is independently selected from the group consisting of unsubstituted $C_{1-12}$alkoxy, unsubstituted $C_{1-8}$alkyl, unsubstituted $C_{6\ or\ 10}$aryl, unsubstituted $C_{7-12}$aralkyl, unsubstituted 5-10 membered heteroaryl, unsubstituted $C_{3-12}$ heteroaralkyl, and unsubstituted 3-10 membered heterocyclyl. In some embodiments, $R^1$, $R^2$, $R^3$ and $R^4$ are each hydrogen. In some embodiments, $R^5$, $R^6$, $R^1$, $R^1$, $R^9$, $R^{10}$, $R^{11}$, $R^{12}$, $R^{13}$, $R^{14}$, $R^{15}$, $R^{16}$, $R^{17}$, $R^{18}$ and $R^{19}$ are each hydrogen. In some embodiments, at least one of $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ is $R^B$. In some embodiments, at least two of $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ are $R^B$. In some embodiments, at least three of $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ are $R^B$. In some embodiments, each $R^B$ is independently selected from the group consisting of unsubstituted $C_{1-12}$alkoxy, substituted $C_{1-12}$alkoxy, unsubstituted $C_{1-8}$alkyl, substituted $C_{1-8}$alkyl, unsubstituted $C_{6\ or\ 10}$aryl, substituted $C_{6\ or\ 10}$aryl, unsubstituted $C_{7-12}$aralkyl, substituted $C_{7-12}$aralkyl, unsubstituted 5-10 membered heteroaryl, substituted 5-10 membered heteroaryl, unsubstituted $C_{3-12}$ heteroaralkyl, substituted $C_{3-12}$heteroaralkyl, unsubstituted 3-10 membered heterocyclyl, and substituted 3-10 membered heterocyclyl. In some embodiments, each $R^B$ is independently selected from the group consisting of unsubstituted $C_{1-12}$alkoxy, unsubstituted $C_{1-8}$alkyl, unsubstituted $C_{6\ or\ 10}$aryl, unsubstituted $C_{7-12}$aralkyl, unsubstituted 5-10 membered heteroaryl, unsubstituted $C_{3-12}$ heteroaralkyl, and unsubstituted 3-10 membered heterocyclyl. In some embodiments, two adjacent $R^B$ groups together with the atoms to which they are attached form an unsubstituted 3-10 heterocyclyl, a substituted 3-10 heterocyclyl, unsubstituted 5-10 membered heteroaryl ring or substituted 5-10 membered heteroaryl ring.

In some embodiments, the pharmaceutical composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in cremes, in lipid compositions, via a catheter, via a lavage, via continuous infusion, via infusion, via inhalation, via injection, via local delivery, or via localized perfusion. The pharmaceutical composition may be formulated for oral, topical, intravenous, or intravitreal administration. In some embodiments, the pharmaceutical composition is formulated as a unit dose.

In yet another aspect, the present disclosure provides methods of treating and/or preventing a disease or a disorder in a patient in need thereof, comprising administering to the patient a composition described herein in an amount sufficient to treat and/or prevent the disease or disorder. In some embodiments, the present disclosure provides methods of treating aneurysms.

Some embodiments provide a method of purifying a compound of Formula (I) comprising: washing a mixture with a solvent to remove substantially all gallic acid or methyl gallate. In some embodiments, the solvent is diethyl ether. In some embodiments, the solvent is selected from the group consisting of methanol, toluene, isopropyl ether, dichloromethane, methyl tert-butyl ether, 2-butanone, and ethyl acetate. In some embodiments, the washing results in a purity of the compound of Formula (I) thereof greater than or equal to 99.10%, 99.20%, 99.30%, 99.40%, 99.50%, 99.60%, 99.70%, 99.80%, 99.90%, 99.91%, 99.92%, 99.93%, 99.4%, 99.95%, 99.96%, 99.97%, 99.98%, or 99.99%.

Some embodiments provide a kit for treating aneurysms, comprising: a compound of Formula (I) having a purity greater than or equal to 99%; and a hydrolyzer. In some embodiments, the hydrolyzer is ethanol. In some embodiments, the hydrolyzer is dimethyl sulfoxide (DMSO). In some embodiments, the hydrolyzer is contrast media. In some embodiments, the kit further comprises a saline solution.

Some embodiments provide a device for treating an aneurysm, comprising: a shaft; a first balloon attached to a first end of the shaft; and a second balloon attached to a second end of the shaft, the second balloon comprising a plurality of pores for delivering a therapeutic agent to the aneurysm. In some embodiments, the first balloon is positioned near a distal end of the shaft for anchoring the device and stopping downstream blood flow, and wherein the second balloon is positioned near a proximal end of the shaft. The second balloon may be configure for stopping retrograde blood flow and/or for displacing blood for the aneurysmal sac, which may improve the efficacy of drug delivery to the aneurysm. In some embodiments, the second balloon is positioned near a distal end of the shaft for anchoring the device and stopping downstream blood flow, and wherein the first balloon is positioned near a proximal end of the shaft for stopping retrograde blood flow. In some embodiments, the device further comprises a third balloon positioned within the second balloon for expanding the second balloon, the third balloon expandable with saline.

Some embodiments provide a method for treating an aneurysm, comprising: positioning a first balloon upstream the aneurysm; positioning a second balloon adjacent the aneurysm; inflating the first balloon to occlude downstream blood flow; expanding the second balloon to occlude retrograde blood flow and/or to displace blood from the aneurysmal sac; and delivering a therapeutic agent to the aneurysm through pores in the second balloon.

Some embodiments provide a method of purifying 1,2,3,4,6-pentagalloyl glucose (PGG) or analogues or derivatives thereof comprising washing the PGG with a solvent to remove substantially all gallic acid or methyl gallate. In some embodiments, the solvent may be or may comprise diethyl ether, toluene, isopropyl ether, dichloromethane, methyl tert-butyl ether, 2-butanone, and/or ethyl acetate. Removing substantially all gallic acid or methyl gallate may result in less than about 0.1%, 0.2%, 0.3%, 0.4%, or 0.5% gallic acid or methyl gallate. The washing may results in a purity of the 1,2,3,4,6-pentagalloyl glucose (PGG) or analogues or derivatives thereof greater than or equal to 99.9%.

Some embodiments provide a kit for treating aneurysms. The kit includes PGG having a purity greater than or equal to 99% and a hydrolyzer. The hydrolyzer may be or may comprise ethanol, dimethyl sulfoxide (DMSO), and/or contrast media. The kit may include a saline solution.

Some embodiments provide a device for treating an aneurysm. The device has a shaft, a first balloon attached to a first end of the shaft, and a second balloon attached to a second end of the shaft. The second balloon includes a plurality of pores for delivering a therapeutic agent to the aneurysm. In some embodiments, the first balloon may be positioned near a distal end of the shaft for anchoring the device and stopping downstream blood flow, and the second balloon may be positioned near a proximal end of the shaft for stopping retrograde blood flow. In some embodiments, the second balloon may be positioned near a distal end of the shaft for anchoring the device and stopping downstream blood flow, and the first balloon may be positioned near a proximal end of the shaft for stopping retrograde blood flow. The device may include a third balloon positioned within the second balloon for expanding the second balloon. The third balloon may be expandable with saline.

Some embodiments provide a catheter for treating an aneurysm. The catheter has an elongate body configured to be introduced into a blood vessel. The elongate body has a proximal end, a distal end, and a main shaft having a lumen extending therethrough. The catheter has a first inflatable balloon coupled to the distal end of the elongate body and having an interior volume in fluid communication with a first inflation lumen. The catheter has a second inflatable balloon coupled to the elongate body proximally to the first inflatable balloon and having an interior volume in fluid communication with a second inflation lumen. The second inflatable balloon circumferentially surrounds the elongate body. The second inflatable balloon has a plurality of pores disposed on a surface of the second inflatable balloon configured to place the interior volume of the second inflatable balloon in fluid communication with an intravascular environment of the blood vessel.

In some embodiments, the main shaft may extend through the second inflatable balloon. The distal end of the main shaft may form the distal end of the elongate body. The first inflation lumen and the second inflation lumen may be formed within the main shaft. The elongate body may include a second shaft having a lumen extending therethrough. The second shaft may be disposed within the lumen of the main shaft. The first inflatable balloon may be coupled to a distal end of the second shaft and the second inflatable balloon may be coupled to a distal end of the main shaft. The lumen of the main shaft may be the second inflation lumen. The lumen of the second shaft may be the first inflation lumen. The elongate body may extend through the interior volume of the second inflatable balloon. The second inflatable balloon may be generally toroidal forming an annular interior volume that surrounds the elongate body. The elongate body may have an intermediate shaft segment positioned between a proximal end of the first inflatable balloon and a distal end of the second inflatable balloon. The intermediate shaft segment may include the main shaft and/or the second shaft. A separation distance between the first inflatable balloon and the second inflatable balloon may be fixed or may be adjustable. The catheter may have a lumen configured to be placed in fluid communication with a volume of the intravascular environment between the first inflatable balloon and the second inflatable balloon.

The pores may be disposed on a central portion of the second inflatable balloon. The pores may be disposed on a distal portion of the second inflatable balloon. The pores may not be disposed on a proximal portion of the second inflatable balloon. The pores may not be disposed on any portion of the second inflatable balloon proximal to a maximum expanded diameter of the balloon in an inflated configuration. The maximum expanded diameter of the second inflatable balloon may be greater than the maximum expanded diameter of the first inflatable balloon. The length of the expanded second inflatable balloon may be greater than the length of the expanded first inflatable balloon.

The catheter may include a third inflatable balloon disposed within the interior volume of the second inflatable balloon. The third inflatable balloon may have an interior volume in fluid communication with a third inflation lumen. Expansion of the third inflatable balloon may be configured to at least partially expand the second inflatable balloon. Expansion of the third inflatable balloon may be configured to facilitate expulsion of at least a partial volume of inflation fluid disposed within the interior volume of the second inflatable balloon through the pores into the intravascular environment.

Some embodiments provide a method for treating an aneurysm in a blood vessel of a patient. The method comprises positioning a first balloon upstream the aneurysm, positioning a second balloon adjacent the aneurysm, inflating the first balloon to occlude downstream blood flow, expanding the second balloon to occlude retrograde blood flow, and delivering a therapeutic agent to the aneurysm through pores in the second balloon. In some embodiments, expanding the second balloon comprises introducing an inflation fluid into an interior volume of the second balloon. Delivering the therapeutic agent may comprise introducing a solution comprising the therapeutic agent into an interior volume of the second balloon to expand and/or maintain an expanded state of the second balloon. Inflating the first balloon and expanding the second balloon may create a sealed volume within the blood vessel between the first balloon and the second balloon. Delivering the therapeutic agent may comprise introducing the therapeutic agent into the sealed volume. The therapeutic agent may not be delivered into the blood vessel outside of the sealed volume while the sealed volume is established.

Inflating the first balloon may anchor the first balloon and the second balloon within the blood vessel. Positioning the second balloon adjacent the aneurysm may comprise positioning the second balloon across the aneurysm and expanding the second balloon may create a sealed space between the second balloon and the aneurysm. Positioning the second balloon adjacent the aneurysm may comprise positioning the second balloon along a downstream edge of the aneurysm and expanding the second balloon may create a sealed volume between the first balloon and the second balloon which encompasses the aneurysm. Positioning the second balloon adjacent the aneurysm may comprise positioning the second balloon such that a length of the aneurysm along the blood vessel encompasses an entire length of the second balloon. Inflating the first balloon may occur prior to expanding the second balloon. Expanding the second balloon and/or maintaining the second balloon in an expanded state may comprise maintaining a pressure within an interior volume of the second balloon greater than a diastolic blood pressure of the patient and less than a systolic blood pressure of the patient. Expanding the second balloon and delivering the therapeutic agent through the pores may comprise introducing a solution into an interior volume of the second balloon. The solution may be introduced at a first volumetric flow rate to expand the second balloon and at a second volumetric flow rate to deliver the therapeutic agent through the pores. The first volumetric flow rate may be greater than or equal to the second volumetric flow rate.

Blood flow may be occluded within the blood vessel for no longer than approximately 3 minutes. At least 1 mL of solution comprising the therapeutic agent may be delivered while downstream blood flow and retrograde blood flow vessel is occluded. Expanding the second balloon may comprise inflating a third balloon disposed within an interior volume of the second balloon. Delivering the therapeutic agent may comprise inflating a third balloon disposed within an interior volume of the second balloon to force a volume of solution comprising the therapeutic agent within the interior volume of the second balloon through the pores. The therapeutic agent may comprise pentagalloyl glucose (PGG). The PGG may be at least 99.9% pure. The therapeutic agent may be substantially free of gallic acid or methyl gallate.

BRIEF DESCRIPTION OF THE DRAWINGS

The features and advantages of the systems, devices, and methods described herein will become apparent from the following description, taken in conjunction with the accompanying drawings. These drawings depict only several embodiments in accordance with the disclosure and are not to be considered limiting of its scope. In the drawings, similar reference numbers or symbols typically identify similar components, unless context dictates otherwise. The drawings may not be drawn to scale.

FIG. 2A depicts a delivery catheter in which the downstream balloon is coupled at a proximal end to the distal end of the main shaft and at the distal end to the secondary shaft, and in which the upstream balloon is coupled to the distal end of the secondary shaft. FIG. 2B depicts a delivery catheter in which the downstream balloon is a generally toroidal balloon coupled to the distal end of the main shaft and surround the secondary shaft, and in which the upstream balloon is coupled at proximal and distal ends to the secondary shaft. FIG. 2B also illustrates a supplemental internal lumen in fluid communication with a sealed volume created between the upstream balloon and the downstream balloon and a lead segment positioned on a distal end of the delivery catheter. FIG. 2C depicts a delivery catheter in which the downstream balloon is coupled at proximal and distal ends to the main shaft, and in which the upstream balloon is coupled at proximal and distal ends to the secondary shaft. FIG. 2C also illustrates a secondary shaft having a central lumen which is open at the distal end of the delivery catheter and in fluid communication with the intravascular environment.

FIG. 3A depicts a downstream balloon that is longer in length than the aneurysm and which is expanded to create a sealed space between the downstream balloon and the blood vessel wall of the aneurysm. FIG. 3A also depicts pores being disposed on a central portion of the downstream balloon. FIG. 3B schematically depicts a downstream balloon expanded to fluidly seal a downstream edge of the aneurysm, creating a sealed volume between the downstream balloon and the upstream balloon. FIG. 3B also depicts pores being disposed on a distal portion of the downstream balloon. FIG. 3C depicts a downstream balloon that is shorter in length than the aneurysm and which is expanded to bring the downstream balloon into contact with the blood vessel wall of the aneurysm.

FIGS. 4A-4C schematically depict various examples of a delivery catheter comprising an inner balloon disposed within the downstream balloon. FIG. 4A depicts the inner balloon coupled at a proximal end to the distal end of the main shaft and coupled at a distal end to the secondary shaft. FIG. 4B depicts the inner balloon coupled at proximal and distal ends to the secondary shaft. FIG. 4C depicts the inner balloon coupled at proximal and distal ends to the main shaft.

DETAILED DESCRIPTION

Figure 1B:
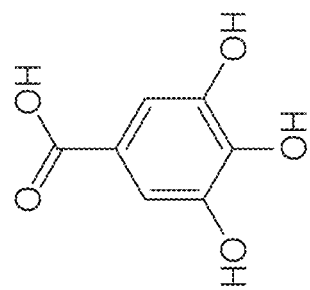
FIG. 1B depicts the chemical structure of gallic acid, a common toxic impurity in the production of PGG.
Figure 1C:
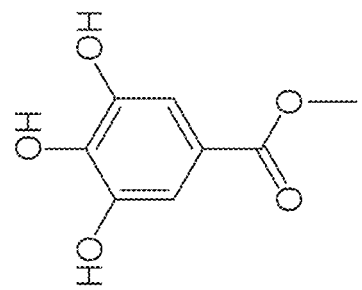
FIG. 1C depicts the chemical structure of methyl gallate, a common toxic impurity in the production of PGG.
Figure 1A:
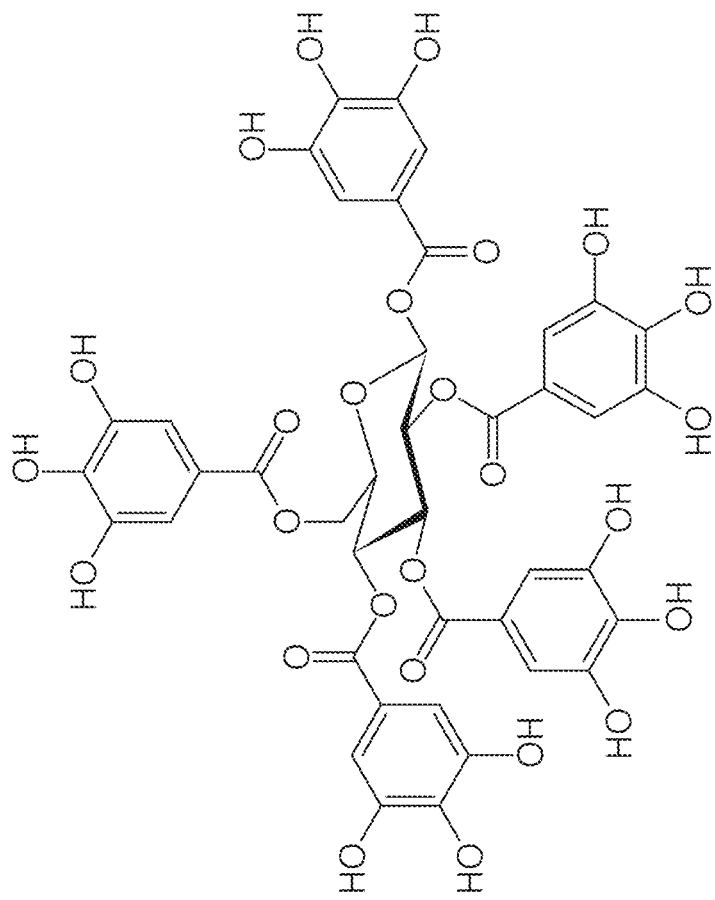
FIG. 1A depicts the chemical structure of 1,2,3,4,6-pentagalloyl glucose (PGG) in a preferred embodiment.

Disclosed herein are methods of purifying and delivering pentagalloyl glucose (PGG). In preferred embodiments, the PGG may be 1,2,3,4,6-pentagalloyl glucose as depicted in FIG. 1A. However, PGG may refer to any chemical structure encompassed by Formula (I), disclosed elsewhere herein. Further disclosed herein, are devices for delivery of PGG or another therapeutic agent to a blood vessel or other body lumen, although the treatment with PGG disclosed herein is not necessarily limited to delivery with these devices. Additionally, the devices disclosed herein may be used to delivery any suitable therapeutic agent to any suitable site of a subject. PGG may be delivered to a subject to treat any one or more of various indications.

In a preferred embodiment, PGG may be delivered to the blood vessel wall for treatment of an aneurysm, such as an abdominal aortic aneurysm. Without being limited by theory, the delivery of PGG to the blood vessel wall where an aneurysm has formed may stabilize the aneurysm by cross-linking, at least transiently, the elastin proteins within the extracellular matrix of the connective tissue of the blood vessel wall. Treatment of the blood vessel with an elastin-stabilizing compound, such as PGG, may increase the mechanical integrity of the blood vessel where the aneurysm is present. Treatment with PGG may prevent, inhibit, and/or slow the growth of an aneurysm and further thinning of the blood vessel wall and may prevent, inhibit, reduce the likelihood of, and/or delay the risk of rupture of the aneurysm. In some instances, treatment with PGG may facilitate natural healing of the aneurysm by mechanically stabilizing the aneurysm. In some implementations, treatment with PGG may be used prior to, after, and/or concurrently with other interventional treatment of an aneurysm, such as surgical intervention. In some implementations treatment of PGG may be particularly suitable for treating abdominal aortic aneurysms between approximately 4-5 cm in diameter. Treatment of an abdominal aortic aneurysm may, in some cases, delay the need for more traditional invasive therapies by at least about 10 years.

In other applications, PGG may be used to treat aneurysms besides abdominal aortic aneurysms, including peripheral and neural aneurysms. PGG may be delivered to these aneurysms by the same device as described herein with respect to abdominal aortic aneurysms or one similar thereto or may be delivered using another device or route of administration. For instance, in some embodiments, PGG, particularly a high purity PGG as disclosed herein, may be suitable for direct injection into the bloodstream or into another tissue for treatment of other indications. In some embodiments, PGG may be used to stabilize and/or facilitate closure of vascular access holes created by puncturing a blood vessel to access the blood stream for drawing blood and/or for therapeutic treatment via the vasculature, such as delivery of a catheter. PGG may promote closure of the vascular access site by means to those for treating an aneurysm. The PGG may stabilize the blood vessel wall around the access hole by crosslinking elastin within the blood vessel, which may promote or accelerate natural healing. PGG may be applied to the access hole via intravascular application and/or by applying PGG directly to the skin over the vascular access hole. PGG may have beneficial effects toward wound closure in connective tissue comprising elastin outside the blood vessel wall, such as the superficial layers of skin above the vascular access hole, including subcutaneous tissue. Similarly, PGG may be used to treat musculoskeletal conditions, including the treatment of injured ligaments and/or tendons, by crosslinking the elastin within the connective tissue. PGG may be used to coat vascular stents and/or grafts. PGG delivered to blood vessel walls after angioplasty, for instance, may structurally stabilize the blood vessel wall and help prevent or inhibit restenosis of the blood vessel. Additionally, PGG may be used to treat and/or prevent aortic dissection. Treatment of an aortic dissection with PGG may help close a tear in the media layer of the blood vessel, may prevent propagation of the tear along the blood vessel wall, and/or may stabilize the tear promoting natural healing. In some instances, PGG may be delivered to an aortic dissection using the delivery device described herein or one similar thereto.

Purified PGG

The concentrations of PGG which may be safely delivered to a patient may be generally proportional to the purity of the PGG. For example, gallic acid, depicted in FIG. 1B, and methyl gallate, depicted in FIG. 1C, are common cytotoxic impurities which may be removed from a source batch of PGG during the purification process. Eliminating the presence of or reducing the concentration of toxic impurities from the delivered PGG may allow higher concentrations of the PGG to be delivered due to the mitigation of the toxic side effects of impurities commonly found in isolated PGG. For instance, studies have shown that substantially 100% pure PGG may be safely delivered at concentrations up to approximately 0.330% (w/v), 95% pure PGG may be safely delivered at concentrations up to approximately 0.125% (w/v), and 85% pure PGG may be safely delivered at concentrations up to approximately 0.06% (w/v). Delivery of PGG in higher concentrations may enhance the amount of uptake of PGG by the target tissue which may increase the efficacy of the PGG treatment. Delivery of PGG in higher concentrations may increase the rate of uptake of PGG by the tissue allowing the same amount of uptake in shorter delivery times. Reducing or minimizing the delivery time may be advantageous for reducing the overall treatment time, and particularly the duration of time for which a blood vessel, such as the aorta, is potentially occluded, as described elsewhere herein. Minimization of the treatment time and particularly the duration of blood occlusion may improve the safety and convenience of the treatment procedure and improve patient outcomes.

Unpurified or partially purified PGG may be obtained from any suitable source and purified according to the methods described herein for use as a therapeutic agent. PGG may be extracted from naturally occurring plants such as pomegranate or Chinese gall nut. Extraction and/or isolation methods may entail solvolysis (for example, methanolysis) of tannin or derivative polyphenols as is known in the art. A PGG hydrate is commercially available from Sigma Aldrich (St. Louis, Missouri) at purities greater than or equal to 96%, as confirmed by HPLC. PGG obtained from these sources may undergo additional purification according to the methods described herein to arrive at substantially pure PGG at the purity levels described elsewhere herein.

In some embodiments, PGG is purified by washing a starting batch of PGG (e.g, less than 99% pure) with a solvent. In preferred embodiments, the solvent may comprise diethyl ether. In other embodiments, the solvent may comprise methanol, toluene, isopropyl ether, dichloromethane, methyl tert-butyl ether, 2-butanone, and/or ethyl acetate. In some embodiments, the washing solution may comprise mixtures of the solvents described herein and/or may be mixed with additional solvents. In some embodiments, the starting batch of PGG may be dissolved into a solution. In some embodiments, the PGG may be dissolved in dimethyl sulfoxide (DMSO). In some embodiments, the PGG may be dissolved in any solvent in which the PGG is soluble and which is not miscible with the washing solution. The PGG solution may be mixed with the washing solution in a flask and the PGG solution and washing solution may be allowed to separate over time. The washing solution may subsequently be separated from the PGG solution, such as by draining the denser solution from the flask or by decanting the less dense solution. In some embodiments, the mixture of the washing solution and PGG solution may comprise a volume-to-volume ratio of at least about 1:1, 1.5:1, 2:1, 3:1, 4:1, 5:1, or 10:1 washing solution-to-PGG solution. In some embodiments, the washing step may be repeated at least 1, 2, 3, 4, 5, 6, 7, 8, 9, or 10 times. In some embodiments, the washed PGG solution may be evaporated upon purification to precipitate the PGG into a dry (solid) form. In some embodiments, the PGG may remain dissolved, but the volume of the solution may be increased or decreased (for example, by evaporation). In some embodiments, the starting batch of PGG may be in a dry (solid) form. The PGG may be crystalized. In some embodiments, the PGG may be lyophilized. In some embodiments, the PGG may be precipitated from solution. In some embodiments, the starting batch of PGG may be placed on filter paper and the washing solution poured over the filter paper into a waste flask. The filtration may be facilitated by application of a vacuum to the waste flask (vacuum filtration). Residual washing solution may be evaporated from the purified batch of PGG. In some embodiments, the washing step may be repeated at least 1, 2, 3, 4, 5, 6, 7, 8, 9, or 10 times. The purity of the PGG may increase with each wash. The washing procedure may be repeated until a desired level of purity is attained.

In some embodiments, washing the PGG may result in a purity of at least approximately 99.000%, 99.500%, 99.900%, 99.950%, 99.990%, 99.995%, or 99.999% purity. Purity may be measured as the percent mass (w/w) of PGG in a sample. Purity of the PGG may be measured by any standard means known in the art including chromatography and nuclear magnetic resonance (NMR) spectroscopy. In some embodiments, the purified PGG may comprise no more than approximately 0.001%, 0.005%, 0.01%, 0.05%, 0.1%, 0.2%, 0.3%, 0.4%, 0.5%, 0.6%, 0.7%, 0.8%, 0.9%, or 1% gallic acid. In some embodiments, the purified PGG may comprise no more than approximately 0.001%, 0.005%, 0.01%, 0.05%, 0.1%, 0.2%, 0.3%, 0.4%, 0.5%, 0.6%, 0.7%, 0.8%, 0.9%, or 1% methyl gallate.

Kits for Delivery of PGG

PGG may be prepared in a solution for delivery as a therapeutic agent to a patient. The PGG may comprise a purity described elsewhere herein. The PGG may have been purified by the methods disclosed elsewhere herein or may have been purified by other means. In some embodiments, the PGG may be dissolved in a hydrolyzer for subsequent delivery to a patient. The hydrolyzer may comprise any solvent or mixture of solvents in which PGG is readily soluble and which is miscible with water. In some embodiments, the hydrolyzer may be ethanol. In some embodiments, the hydrolyzer may be dimethyl sulfoxide (DMSO). In some embodiments, the hydrolyzer may be contrast media. In some embodiments, the hydrolyzer may be a mixture of ethanol, DMSO, and/or contrast media in any proportions. The hydrolyzer may facilitate the dissolution of PGG into a larger aqueous solution, in which the PGG would not normally be soluble at the same concentration without first being dissolved into the hydrolyzer. The PGG may ultimately be dissolved into a non-toxic aqueous solution suitable for delivery, such as intravascular delivery, to a patient. The aqueous solution may be a saline solution, as is known in the art, or another aqueous solution comprising salts configured to maintain physiological equilibrium with the intravascular environment. The volumetric ratio of the hydrolyzer to the saline solution may be minimized, while maintaining a sufficient volume of hydrolyzer to fully dissolve the desired amount of PGG, to minimize any harmful or toxic effects of the hydrolyzer on the patient, particularly when delivered intravascularly. In some embodiments, the volume-to-volume ratio of saline to hydrolyzer may be no less than about 10:1, 25:1, 50:1, 75:1, 100:1, 200:1, 300:1, 400:1, 500:1, 600:1, 700:1, 800:1, 900:1, or 1000:1. The total volume of the hydrolyzer and saline mixture (including any other additional components) may be configured to prepare the PGG to a desired therapeutic concentration, such as the concentrations described elsewhere herein. In some embodiments, the PGG may be dissolved into the saline or other aqueous solution without a hydrolyzer. In some embodiments, the saline may be warmed (e.g., to above room temperature or above physiological temperature) to dissolve or help dissolve the PGG (or other therapeutic agent). For instance, the saline may be warmed to at least about 25° C., 30° C., 35° C., 40° C., 45° C., 50° C., 55° C., or 60° C. prior to dissolving the PGG. In some implementations, the therapeutic solution may be raised to and/or maintained at an elevated temperature (e.g., physiological temperature) during delivery.

In some embodiments, PGG (for example, purified PGG) for a therapeutic treatment, including but not limited to those described elsewhere herein, may be provided in a kit comprising the components necessary to prepare the PGG for delivery in a therapeutic solution. In some embodiments, the kit may comprise the PGG in a solid (dry) form, the hydrolyzer, and/or the saline solution. The kit may be configured to optimize the storage conditions of the PGG, for short or long-term storage. In some embodiments, the kit may be configured to store the PGG for up to at least 1 week, 2 weeks, 3 weeks, 4 weeks, 1 month, 2 months, 3 months, 4 months, 5 months, 6 months, 1 year, 2 years, or 3 years. The kit may comprise one or more aliquots of each component in pre-measured amounts or volumes. Each component may be provided in a sealed vial, tube, or other container as is known in the art. The containers may each comprise plastic and/or glass. The containers may be configured (for example, tinted or covered) to protect the components from light and/or other radiation. In some embodiments, the kit may be configured for shipping. For example, the components may be contained in a box or other container including desiccants and/or may be configured for temperature control. In some embodiments, the PGG and/or other components may be supplied in a container that has been purged of air (particularly, oxygen). The component may be stored under vacuum or may be purged with an inert gas, such as nitrogen or argon. In some embodiments, the PGG may be mixed with an antioxidant or other stabilizer, in addition to or alternatively to purging the air. In some embodiments, the antioxidant may comprise Vitamin C, Vitamin E, and/or any other antioxidant or stabilizer which is known in the art and is safe for treatment. In some embodiments, the PGG may be provided already dissolved in the hydrolyzer to a predetermined concentration. In some embodiments, the volume of saline provided may be configured to prepare the PGG at a desired therapeutic concentration. In some embodiments, the volume of saline may be configured to prepare the PGG at a maximal therapeutic concentration, such that a user may dilute the PGG with additional solvent to the desired therapeutic concentration. In some embodiments, the total volume of saline may be configured to prepare the PGG at a concentration below the desired concentration and the user may use only a portion of the volume of the saline to prepare the PGG to the desired concentration. The container of saline may have volume indicators for facilitating measurement of the saline. In some embodiments, the saline may be provided in a plurality of aliquots having the same and/or different volumes, which may allow the user to select an aliquot of a desired volume to prepare the PGG at a desired concentration and/or combine various volumes to prepare the PGG at a desired concentration. In some embodiments, the kit may comprise one or more additional components. For example, the kit may comprise a contrast agent for mixing with the therapeutic PGG solution for allowing indirect visualization of the therapeutic solution, as described elsewhere herein.

Delivery Devices

In some implementations, PGG and/or other therapeutic agents or medicaments, including but not limited to those described elsewhere herein, may be delivered to the site of an aneurysm, such as an abdominal aortic aneurysm, or to an isolated section of a blood vessel via a catheter device as described herein. Abdominal aortic aneurysms are generally found in the abdominal aorta downstream of the renal arteries, above where the aorta splits into the iliac arteries. The delivery catheter may be specifically configured (for example, dimensioned), for delivery of a therapeutic agent to an abdominal aortic aneurysm.

Figure 2A:
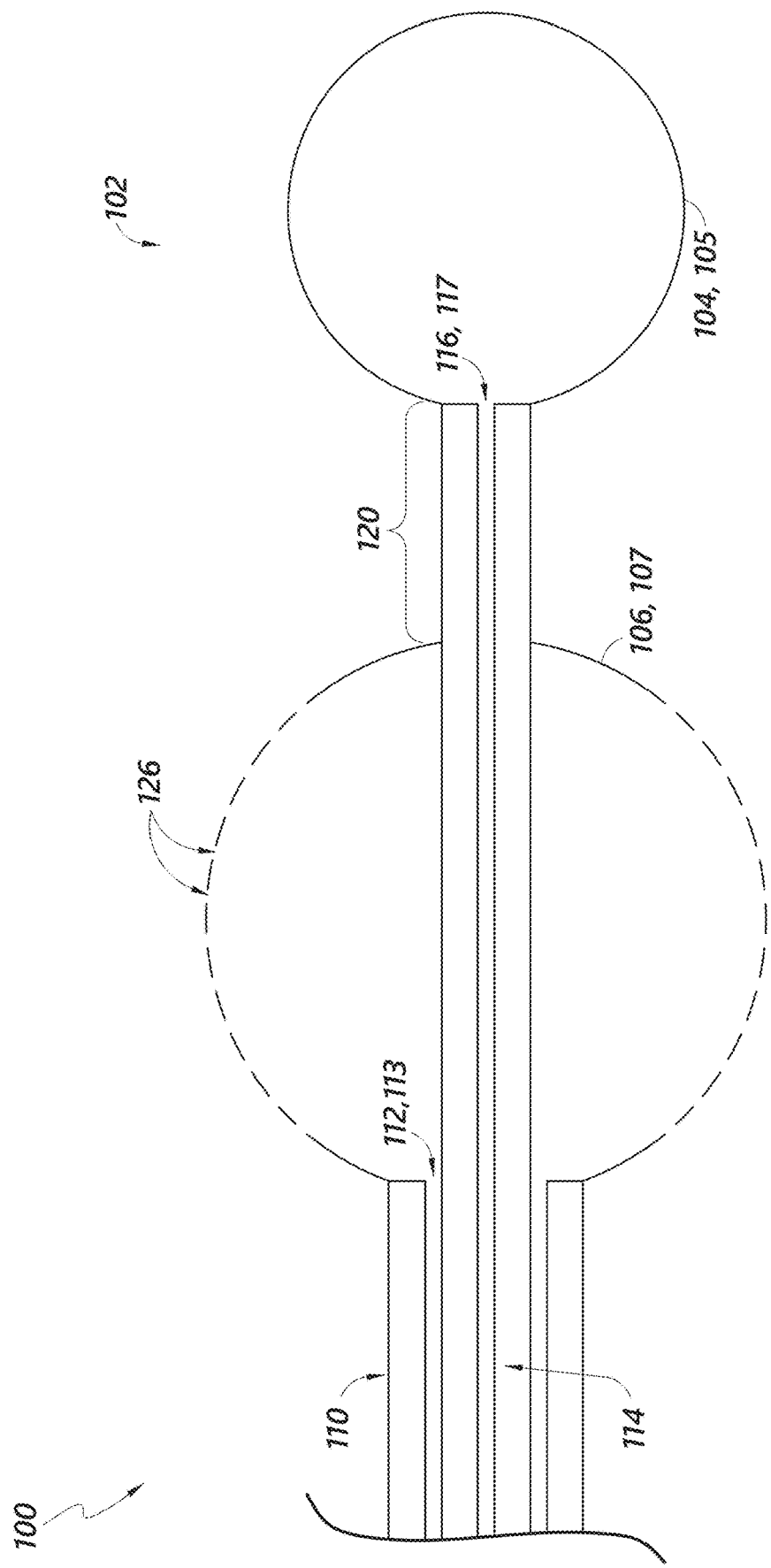
FIGS. 2A-2C schematically depict various examples of a delivery catheter for the delivery of PGG or another therapeutic agent to a blood vessel.

FIG. 2A schematically depicts an example of a delivery catheter 100.

The delivery catheter 100 may comprise a proximal end (not shown), configured to remain outside of the body during use, and a distal end 102, configured to be positioned within the blood vessel near (generally distal to) the target aneurysm or target site or section of blood vessel to be treated. The delivery catheter 100 may comprise a main shaft 110, an upstream expandable member 104 and a downstream expandable member 106. The delivery catheter 100 may have a longitudinal axis extending from the downstream expandable member 106 to the upstream expandable member 104. The upstream expandable member 104 may be positioned at or near the distal end 102 of the delivery catheter 100 and the downstream expandable member 106 may be positioned proximally to the upstream expandable member 104. Such a configuration is useful for introduction of the delivery catheter 100 from a vascular access point downstream of the target aneurysm or blood vessel location. For instance, such a configuration is useful for introduction of the delivery catheter 100 through the femoral artery to treat an abdominal aortic aneurysm. In alternative embodiments, the delivery catheter 100 may be configured for introduction from a location upstream the target aneurysm or target site of the blood vessel and the upstream expandable member 104 may be positioned proximally to the downstream expandable member 102 with respect to the delivery catheter.

Each expandable member 104, 106 may comprise an expanded configuration having an expanded radial diameter and an unexpanded configuration having an unexpanded radial diameter, the expanded radial diameter being larger than the unexpanded radial diameter. The length of one or both of the expandable members 104, 106 may increase, decrease, or remain the same upon expansion. The unexpanded diameter of each expandable member 104, 106 may be configured to facilitate insertion of the delivery catheter 100 into the blood vessel. The unexpanded diameters may each be less than, approximately the same as, or larger than an inner diameter and/or outer diameter of the main shaft 110. The expanded diameter of each expandable member 104, 106 may be configured to occlude the target blood vessel and may be the same as or larger than the diameter of the target blood vessel (for example, the abdominal aorta). In some embodiments, one or both of the expandable members 104, 106 may be operable at intermediate diameters between the unexpanded and fully expanded diameter. The unexpanded diameter of the upstream expandable member 104 may be the same as or different from the unexpanded diameter of the downstream expandable member 106. Similarly, the expanded diameter of the upstream expandable member 104 may be the same as or different from the expanded diameter of the downstream expandable member 106.

In various embodiments, the upstream expandable member 104 may be an inflatable balloon 105, as shown in FIG. 2A. In various embodiments, the downstream expandable member 106 may be an inflatable balloon 107, also shown in FIG. 2A. The inflatable balloons 105, 107 may comprise an elastic material forming an expandable membrane as is known in the art and may be configured to expand upon pressurization from an inflation fluid (for example, a gas or a liquid, such as saline). The balloon material may be biocompatible. In some embodiments, the upstream expandable member 104 and/or the downstream expandable member 106 may be expandable through means other than or in addition to inflation. For example, one or both of the expandable members 104, 106 may comprise radially expandable frames. The expandable frames may comprise a shape memory material (for example, a nickel titanium alloy (nitinol)) and/or may be configured to self-expand. One or both of the expandable members 104, 106 may be configured to self-expand upon release of a constraining mechanism, such as an outer sheath surrounding the expandable member, which may, for instance, be proximally withdrawn to allow self-expansion of the expandable member. In some embodiments, one or both of the expandable frames may be configured to be mechanically expanded, such as by a push wire or pull wire extending through an internal lumen of the delivery catheter 100. The expandable frames may be fixed or coupled to a surrounding fluid impermeable covering or coating such that the expandable members 104, 106 may be configured to occlude fluid flow as described elsewhere herein.

The main shaft 110 of the delivery catheter 100 may extend from the proximal end of the delivery catheter 100 to the downstream balloon 107 (or other downstream expandable member 106). The main shaft 110 may comprise a length and a diameter configured to facilitate navigation of the distal end 102 of the delivery catheter 100 to the target site, which may depend on the particular application and/or vascular access site. In some embodiments, the diameter may vary over a length of the main shaft 110 and/or any internal components, including internal shafts described elsewhere herein. For example, the diameter may decrease in a proximal to distal direction causing a distal portion of the delivery catheter 100 to be more flexible than a proximal portion. As shown in FIG. 2A, the downstream balloon 107 may be attached to a distal end of the main shaft 110. The main shaft 110 may have a first central lumen 112. The main shaft 110 may be generally tubular having a sidewall forming the first inflation lumen central lumen 112. The first central lumen 112 may serve as a first inflation lumen 113 for inflating and/or deflating the downstream balloon 107. The first inflation lumen 113 may be in fluid communication with an interior volume of the downstream balloon 107. An inflation fluid (for example, saline) may be introduced from a proximal end of the delivery catheter 100 through the first inflation lumen 113 into the interior volume of the downstream balloon 107 for inflating or expanding the balloon 107 and removed (for example, aspirated from the balloon 107) through the first inflation lumen 113 to de-inflate the balloon 107. The proximal end of the first inflation lumen 113 and/or any other inflation lumens described herein may each be in fluid communication with a source of pressurized inflation fluid, such as a syringe, an IV bag, a fluid pump, etc. One or more of the inflation lumens and/or balloons described herein may be in fluid communication with one or more pressure sensors for monitoring pressure levels within the internal lumens and/or the balloons with which they are in fluid communication. In some embodiments in which the downstream expandable member 106 comprises an expandable frame, a pull wire or push wire may extend through the first inflation lumen 113 for actuating the expansion or compression of the downstream expandable member 106.

A secondary shaft 114 may extend from a proximal end of the delivery catheter 100 to the upstream balloon 105 (or other upstream expandable member 104). As shown in FIG. 2A, the upstream balloon 105 may be attached to a distal end of the secondary shaft 114. In some embodiments, the secondary shaft 114 may extend through the first central lumen 112. The secondary shaft 114 may comprise a secondary central lumen 116. The secondary shaft 116 may be generally tubular having a sidewall forming the secondary central lumen 116. The second central lumen 116 may serve as a second inflation lumen 117 for inflating and/or deflating the upstream balloon 105. The secondary inflation lumen 116 may be in fluid communication with an interior of the upstream balloon 105. An inflation fluid (for example, saline) may be introduced from a proximal end of the delivery catheter 100 through the secondary inflation lumen 117 into the interior volume of the upstream balloon 105 for inflating or expanding the balloon 105 and removed (for example, aspirated from the upstream balloon 105) through the secondary inflation lumen 117 to de-inflate the upstream balloon 105. In some embodiments in which the upstream expandable member 104 comprises an expandable frame, a pull wire or push wire may extend through the secondary inflation lumen 117 for actuating the expansion or compression of the upstream expandable member 104.

In some embodiments, as shown in FIG. 2A, the secondary shaft 114 may extend through the first central lumen 112. In some embodiments, the secondary shaft 114 may be freely disposed within the first central lumen 112 in a substantially concentric manner. In some embodiments, the secondary shaft 114 may be substantially coaxial with respect to the first central lumen 112. A substantially annular lumen may be formed between the inner diameter of the sidewall of the main shaft 110 and the outer diameter of the sidewall of the secondary shaft 114. Alternatively, the secondary shaft 114 may be coupled to or formed integrally with the inner diameter of the sidewall of the main shaft 110. The distal end of the secondary shaft 114 may extend or be configured to be extendable distally beyond the distal end of the main shaft 110. The secondary shaft 114 may extend through a central portion of the downstream balloon 107 (or other downstream expandable member 105).

In some embodiments, as depicted in FIG. 2A, the secondary shaft 114 may extend through the interior of the downstream balloon 107. The downstream balloon 107 may comprise an expandable membrane having a proximal end and a distal end. The proximal end of the expandable membrane may be coupled to (for example, at or near) the distal end of the main shaft 110. The distal end of the expandable membrane may be coupled to the secondary shaft 114 at a point proximal to the upstream balloon 105. The proximal and distal ends of the expandable membrane may be coupled to main shaft 110 and the secondary shaft 114 to form fluid-tight seals around the outer diameters of the shafts 110, 114, allowing inflation fluid to pressurize the interior volume of the downstream balloon 107 and the expandable membrane to expand radially outward between the proximal and distal ends of the expandable membrane upon the introduction of the inflation fluid.

Figure 2B:
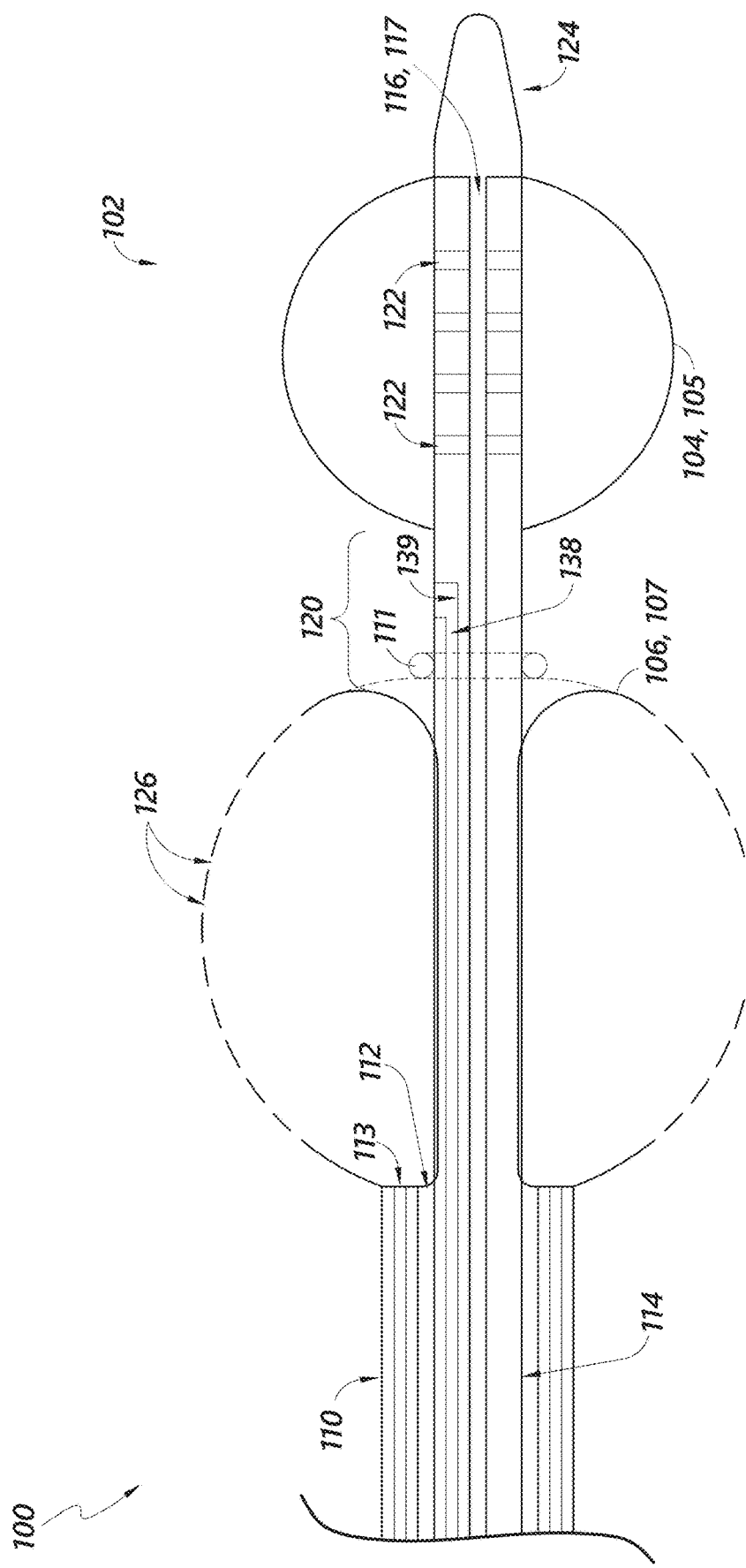

In some embodiments, the downstream balloon 107 may have a generally toroidal configuration, as schematically illustrated in FIG. 2B, in which the expandable membrane of the downstream balloon 107 has an outer surface and an inner surface, the inner surface forming a closed circumference defining a central hole through which the secondary shaft 114 may extend. The downstream balloon 107 may define an annular interior volume configured to be pressurized by introduction of inflation fluid from the first inflation lumen 113. In some embodiments, the downstream balloon 107 may be coupled to the distal end of the main shaft 110 such that it is in fluid communication with the annular shaped lumen 112 as described with respect to FIG. 2A. In some embodiments, the downstream balloon 107 may be coupled to an outer circumference of the main shaft 110 and in fluid communication with an inflation port formed in the sidewall of the main shaft 110, as described elsewhere herein. In some embodiments, the generally toroidal downstream balloon 107 may comprise a distal coupling, such as a coupling ring 111, configured to couple a distal end of the downstream balloon 107 to the main shaft 110, the secondary shaft 114, or another component of the delivery catheter 100. The distal coupling may orient the downstream balloon 107 in a proper configuration with respect to the delivery catheter 100. The distal coupling may rigidly fix the downstream balloon 107 to the coupled component (for example, secondary shaft 114) or it may allow the coupled component to axially translate along the longitudinal axis with respect to the distal end of the downstream balloon 107, as described elsewhere herein. In some embodiments, the inner surface of the expandable membrane of the downstream balloon 107 may be coupled to (for example, adhered via an adhesive) an outer diameter of the main shaft 110, the secondary shaft 114, and/or another component of the delivery catheter 100.

Figure 2C:
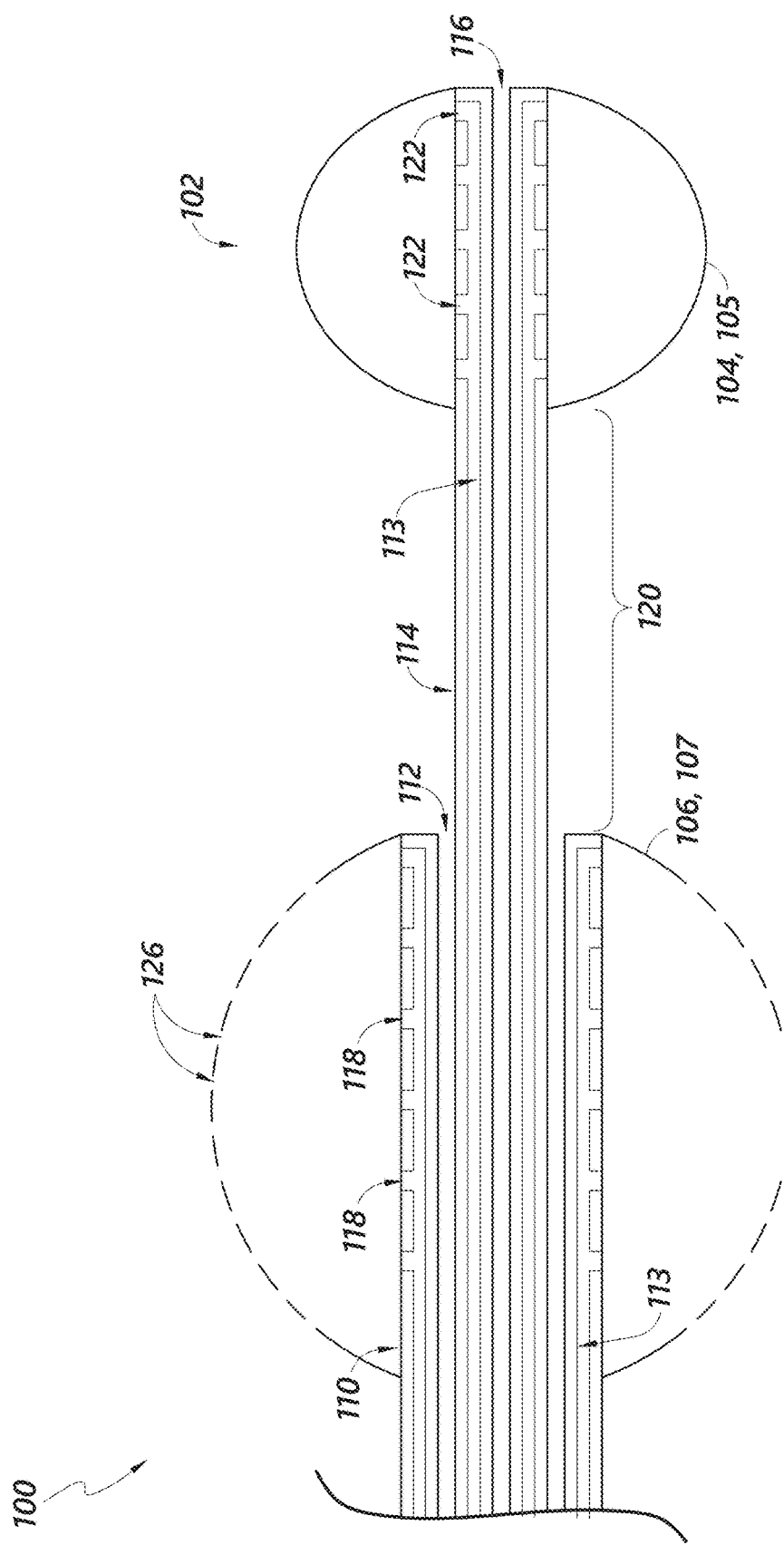

In other embodiments, as depicted in FIG. 2C, the main shaft 110 may extend distally to or beyond the distal end of the expandable membrane of the downstream balloon 107. In such embodiments, both the proximal and distal ends of the expandable membrane may be coupled to the main shaft 110. The first inflation lumen 113 may be formed within the sidewall of the main shaft 110 and may be sealed at the distal end to prevent the escape of the inflation fluid. The first inflation lumen 113 may be formed separately from the first central lumen 112. The first inflation lumen 113 may be positioned radially outside of the first central lumen 112. The first central lumen 112 may be configured to receive the secondary shaft 114, as described with respect to FIG. 2A. The main shaft 110 may have one or more inflation ports 118 in fluid communication with the interior volume of the downstream balloon 107 and the first inflation lumen 113. The inflation ports 118 may pass through a sidewall of the main shaft 110. In some embodiments, a plurality of inflation ports 118 may be spaced longitudinally along the main shaft 110 between the proximal and distal ends of the expandable membrane. In some embodiments, a plurality of inflation ports 118 may be spaced radially around the outer diameter of the main shaft 110. The distal end of the main shaft 110 may be positioned at or just beyond the distal end of the downstream balloon 107, as shown in FIG. 2C. In some embodiments, the main shaft 110 may extend to the upstream balloon 105. In some embodiments, the first central lumen 112 may be in fluid communication with a sealed volume 142, described elsewhere herein, formed between the upstream balloon 105 and the downstream balloon 107. In some implementations, the first central lumen 112 may be used to deliver a therapeutic agent into the sealed volume 142 and/or to aspirate fluid from the sealed volume 142, as described elsewhere herein.

The delivery catheter 100 comprises an intermediate shaft segment 120 extending between the downstream balloon 107 and the upstream balloon 105 (or between other expandable members 104, 106) and configured to space the upstream balloon 105 distally from the downstream balloon 107. The intermediate shaft segment 120 may connect the upstream balloon 105 and downstream balloon 107. In some embodiments, such as that described with respect to FIG. 2A, the secondary shaft 114 may form the intermediate shaft segment 120 (or at least an outer component of the intermediate shaft segment 120). In some embodiments, the main shaft 110 may form the intermediate shaft segment 120 (or at least an outer component of the intermediate shaft segment 120) or at least a portion of the length of the intermediate shaft segment 120. In some embodiments, a separate tubular connector (not shown) extending from a distal end of the downstream balloon 107 to a proximal end of the upstream balloon 105 may form the outermost component of the intermediate shaft segment 120 and the main shaft 110 and/or secondary shaft 114 may pass through the tubular connector.

The upstream balloon 105 may comprise an expandable membrane. The expandable membrane of the upstream balloon 105 may comprise the same and/or different material(s) as the expandable membrane of the downstream balloon 107. In some embodiments, such as that shown in FIG. 2A, a proximal end of the expandable membrane may be coupled to (for example, at or near) the distal end of the secondary shaft 114 forming a fluid tight seal with the secondary shaft 114. The expandable membrane may not be further coupled to any portion of the delivery catheter 100 distal to the proximal seal, as shown in FIG. 2A, and the upstream balloon 105 may form the distal-most part of the delivery catheter 100. Introduction of inflation fluid into the interior volume of the upstream balloon 105 may cause the upstream balloon 105 to expand radially and distally. In some embodiments, a proximal end of the upstream balloon 105 may be coupled to a shaft positioned concentrically around the secondary shaft 114, such as the main shaft 110 or a separate tubular connector as described elsewhere herein, rather than to the secondary shaft 114 itself. The main shaft 110 or other component to which the upstream balloon 105 is coupled may be fluidly sealed (for example, between an inner diameter of the main shaft 110 and the outer diameter of the secondary shaft 114) such that inflation fluid introduced into an interior volume of the upstream balloon 105 through the secondary inflation lumen 117 may ed to pressurize the upstream balloon 105.

In some embodiments, such as depicted in FIG. 2C, the expandable membrane of the upstream balloon 105 may form a proximal seal and a distal seal with a shaft or shafts of the delivery catheter 100, similar to the downstream balloon 107 as depicted in FIG. 2C. The proximal end of the expandable membrane may be coupled to a proximal point on the secondary shaft 114 and the distal end of the expandable membrane may be coupled to (for example, at or near) the distal end of the secondary shaft 114 at a point distal to the proximal point. The proximal and distal ends of the expandable membrane may be coupled to the secondary shaft 114 to form fluid-tight seals around the outer diameter of the shaft 114, allowing inflation fluid to pressurize the interior volume of the upstream balloon 105 and the expandable membrane to expand radially outward between the proximal and distal ends of the expandable membrane upon the introduction of the inflation fluid. The second inflation lumen 117 may be formed separately from the second central lumen 116, as depicted in FIG. 2C. The second inflation lumen 117 may be positioned radially outside of the second central lumen 116. The second central lumen 116 may be configured to receive additional components such as guidewires, as described elsewhere herein. In other embodiments, as shown in FIG. 2B, the secondary shaft 114 may be sealed at or near its distal end and the second central lumen 116 may serve as the secondary inflation lumen 117. The secondary shaft 114 may have one or more secondary inflation ports 122 in fluid communication with the interior volume of the upstream balloon 105 and the secondary inflation lumen 117. The secondary inflation ports 122 may pass through a sidewall of the secondary shaft 114. In some embodiments, a plurality of secondary inflation ports 122 may be spaced longitudinally along the secondary shaft 114 between the proximal and distal ends of the expandable membrane. In some embodiments, a plurality of secondary inflation ports 122 may be spaced radially around the outer diameter of the secondary shaft 114. The distal end of the secondary shaft 114 may be positioned at or just beyond the distal end of the upstream balloon 105, as shown in FIG. 2C. In some embodiments, as described elsewhere herein, an additional shaft and/or lumen may extend through the second central lumen 116 of the secondary shaft 114 and may extend distally beyond the secondary shaft 114.

In some embodiments, a lead segment 124, such as a rod, may be positioned at a distal end of the delivery catheter 100, as schematically depicted in FIG. 2B. The lead segment 124 may be coupled to or formed from a distal end of the secondary shaft 114 and/or a distal end of the upstream balloon 105. The lead segment 124 may comprise an atraumatic (for example, rounded)distal tip. The lead segment 124 may facilitate the introduction and navigation of the delivery catheter 100 within the vasculature. In some embodiments, the lead segment 124, may comprise a radiopaque material.

In various embodiments, the delivery catheter may combine or interchange the various features illustrated and/or described with respect to FIGS. 2A-2C. For instance, the configurations of the upstream balloon 105 and/or the downstream balloon 107 in each example may be exchanged.

In some embodiments, the upstream balloon 105 may be configured to anchor the delivery catheter 100 within the vasculature when in an expanded configuration, which may include full or partial expansion. Anchoring the delivery catheter 100 within the vasculature may stably position the downstream balloon 107 and/or other portions of the delivery catheter 100 at an appropriate position within the vasculature adjacent an aneurysm or other target site. The upstream balloon 105 may be configured to occlude blood flow (for example, downstream or antegrade blood flow), at least within a sealed volume between the upstream balloon 105 and downstream balloon 107, when in an expanded configuration. The expandable membrane of the upstream balloon 105 may be sufficiently compliant or conformable to assume the shape of and occlude the target vasculature. In some embodiments, the upstream balloon 105 may be configured to occlude the abdominal aorta.

In some embodiments, the downstream balloon 107 may be configured to occlude blood flow (for example, upstream or retrograde blood flow) when in an expanded configuration. In some embodiments, the downstream balloon 107 may be configured to displace blood from the aneurysmal sac of an aneurysm. For example, in some implementations, the downstream balloon 107 may be aligned with an aneurysm (e.g., the length of the aneurysm may encompass the length of the downstream balloon 107) and inflating or expanding the downstream balloon 107 may displace blood from the volume of the aneurysmal sac. Displacing blood from the aneurysmal sac may improve the efficacy of delivering therapeutic agent to an aneurysm (e.g., through the downstream balloon 107). For instance, the therapeutic agent will not be diluted or will be less diluted by blood within the aneurysmal sac. The expandable membrane of the downstream balloon 107 may be sufficiently compliant or conformable to assume the shape of and occlude the target vasculature. In some embodiments, the downstream balloon 107 may be non-compliant (for example, a bag member having an membrane enclosing an expandable interior volume) or less compliant than the upstream balloon 105. In some embodiments, the downstream balloon 107 may be equally compliant relative to the upstream balloon 105. In some embodiments, the downstream balloon 107 may be configured to occlude the abdominal aorta. In some implementations, the downstream balloon 107 may require a lower threshold pressure to occlude, or fluidly seal, retrograde blood flow if antegrade blood flow has already been stopped. For example, the upstream balloon 105 may require an inflation pressure greater than or equal to the systolic blood pressure to maintain its expanded configuration and the downstream balloon 107 may require a pressure greater than or equal to the diastolic pressure to maintain its expanded configuration. In some implementations, the role of the downstream balloon 107 and the upstream balloon 105 may be reversed, such as if the delivery catheter 100 is introduced from an upstream location.

In some embodiments, the downstream balloon 107 may be configured to deliver a therapeutic agent, such as a PGG solution, to an aneurysm or other target vasculature site. The downstream balloon 107 may be what is known in the art as a weeping balloon. The downstream balloon 107 may comprise a plurality of pores 126 disposed in the expandable membrane of the balloon configured to place the interior volume of the downstream balloon 107 in fluid communication with the intravascular environment. The solution of therapeutic agent may be used as the inflation fluid. The pores 126 may be configured to provide fluid communication between the interior volume of the downstream balloon 107 and the intravascular environment while allowing for pressurization and inflation of the downstream balloon 107. In some embodiments, the size of the pores 126 may increase as the expandable membrane of the downstream balloon expands. The elastic properties of the expandable membrane of the downstream balloon 107 may allow for a continuous expansion of the pore size of the pores 126 as the interior volume of the downstream balloon 107 is increased causing the expandable membrane to stretch. The volumetric flow rate at which the inflation fluid escapes from the interior volume of the downstream balloon 107 into the intravascular environment may increase as the balloon 107 expands. In some embodiments, the pores 126 may allow for a constant or substantially constant volumetric flow rate of fluid across the pores 126 over a range of pressures of the interior volume. The volumetric flow rate out of the downstream balloon 107 may be maximized at a certain levels of pressurization or volumetric flow rates of inflation fluid into the downstream balloon 107. The inflation fluid may be introduced into the interior volume of the downstream balloon 107 at a volumetric flow rate that is greater than the volumetric flow rate at which the inflation fluid flows through the pores 126, such that the downstream balloon 107 may be inflated even while fluid escapes or leaks through the pores 126. In some implementations, the downstream balloon 107 may be inflated using an inflation fluid (for example, saline) that does not comprise the therapeutic agent. The inflation fluid may be switched over to the therapeutic solution or the therapeutic agent may be added to the inflation fluid after the downstream balloon has been inflated and/or the blood vessel has been sealed from retrograde blood flow. Staggering the delivery of the therapeutic agent may conserve the therapeutic agent and/or may prevent, reduce, or minimize the amount of therapeutic agent that is released into the blood stream before the downstream fluid seal is fully formed with the blood vessel.

Figure 3A:
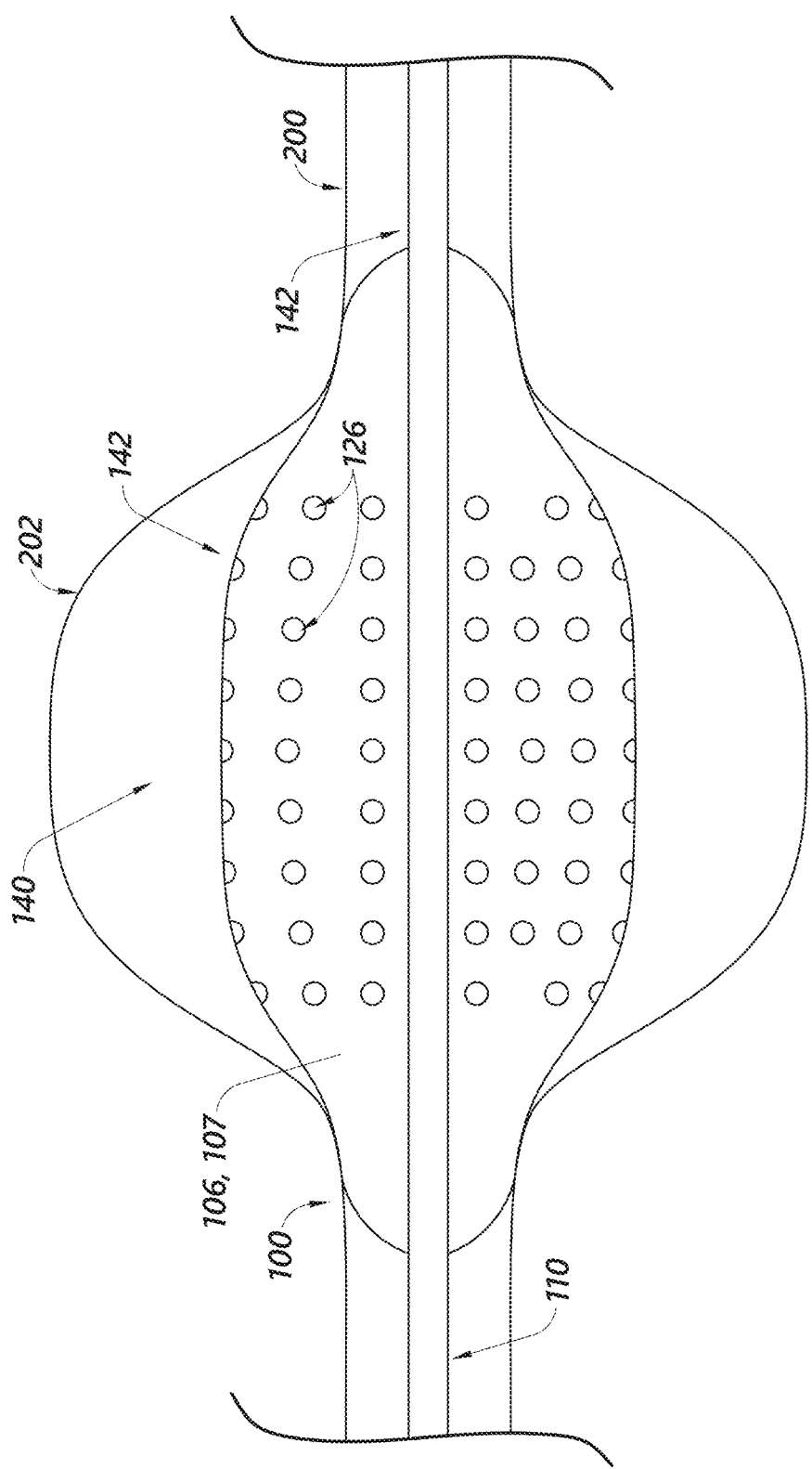
FIGS. 3A-3C schematically depict various examples of a downstream balloon of a delivery catheter expanded within a blood vessel comprising an aneurysm.

The pores 126 of the downstream balloon 107 may be disposed uniformly across the surface or a portion of the surface of the downstream balloon 107. In some embodiments, the pores 126 may be disposed in a central portion of the downstream balloon 107 relative to the longitudinal axis. For example, in some embodiments, the length of the downstream balloon 107 may be configured such that the downstream balloon 107 spans the entire length of an aneurysm 202 or target section of a blood vessel 200 and may create a sealed spaced 140 within the aneurysm or section of blood vessel 200 when the downstream balloon 107 is expanded to a minimal diameter, as illustrated in FIG. 3A. The downstream balloon 107 may form a fluid seal with the inner diameter of the blood vessel at points proximal to and/or distal to the aneurysm. The expandable membrane of the downstream balloon 107 may be configured not to expand radially outward into the sealed space 140 between proximal and distal sealing points, to expand partially into the sealed space 140, or to expand entirely into the sealed space 140 such that the outer surface of the downstream balloon 107 conforms to the shape of the aneurysm 202, depending on the properties (for example, elasticity) of the expandable membrane of the downstream balloon 107. In some embodiments, the downstream balloon 107 may be compliant enough to conform to the shape of the aneurysm 202 and blood vessel wall 200, as depicted in FIG. 3A. In some embodiments, the expanded downstream balloon 107 may somewhat expand the diameter of the blood vessel wall proximate to where the downstream balloon 107 forms fluid seals with the aneurysm 202. The pores 126 may be disposed along a central portion configured to be positioned between a proximal fluid seal and a distal fluid seal such that at least a portion of the pores 126 are in fluid communication with the sealed space 140 and allow delivery of the therapeutic inflation fluid into the sealed space 140 or to a tissue within the sealed space. In some embodiments, any remaining pores 126 of the downstream balloon 107 which are not in fluid communication with the sealed space 140 may be disposed in a configuration on the downstream balloon 107 such that the pores 126 are configured to be pressed against the blood vessel 200 wall in an expanded configuration. When the downstream balloon 107 is expanded, the counter pressure of the blood vessel wall against the outer diameter of the downstream balloon 107 may effectively seal the pores 126 in contact with the blood vessel wall from the intravascular environment such that fluid may not flow at any substantial flow rate through those pores 126. This configuration may prevent or minimize delivery of therapeutic agent into non-targeted volumes of the blood vessel and/or into downstream portions of the blood vessel in which the therapeutic agent may be diffused into the bloodstream within the downstream vasculature. In some embodiments, contact between the therapeutic agent within the inflation fluid with the tissue sealed against the pores 126 may be used to treat the blood vessel wall. In some embodiments a plurality of the pores 126 may be spaced at a high density over an area configured to be pressed into contact with the blood vessel wall, such as a portion of the aneurysm. In some embodiments, the pores 126 may be brought into close proximity (for example, no more than 0.3 mm, 0.2 mm, 0.1 mm, 0.075 mm 0.05 mm, 0.025 mm, 0.001 mm, etc.) to the target blood vessel tissue but not into substantial contact, reducing the volume of the sealed space 140 between the expandable membrane of the downstream balloon 107 and the blood vessel wall.

Figure 3B:
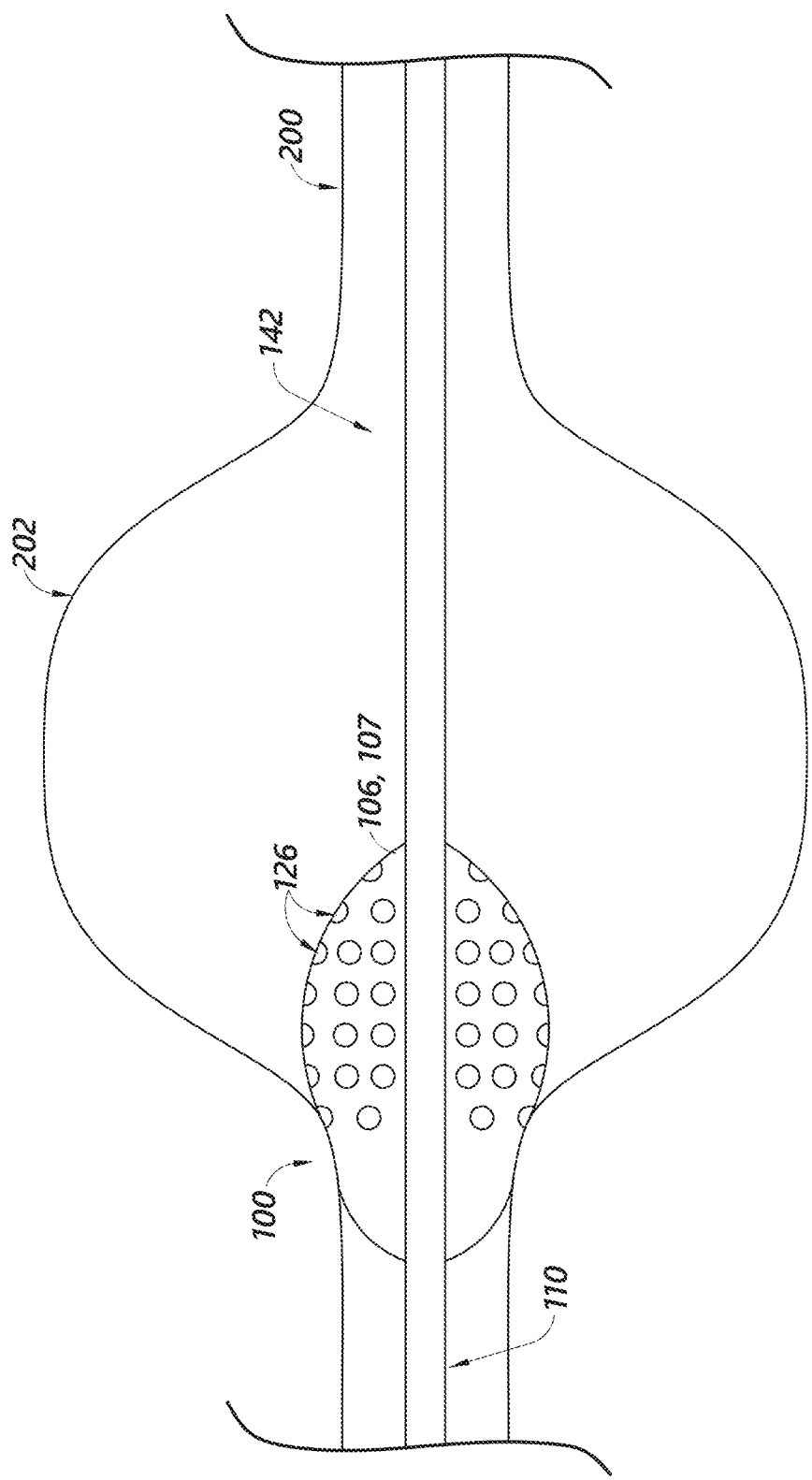

In some embodiments, the pores 126 may be disposed on the downstream balloon 107 along a distal portion of the downstream balloon 107, as illustrated in FIG. 3B. The downstream balloon 107 may be positioned and expanded near a proximal edge of an aneurysm or target section of a blood vessel, causing the balloon to form a fluid seal at a proximal edge of the aneurysm or target section or proximal thereto. The distal portion of the downstream balloon 107 on which the pores 126 are disposed may be positioned distally to the proximal fluid seal formed by the downstream balloon 107, such that at least a portion of the pores 126 are in fluid communication with a sealed volume 142 between the proximal seal formed by the downstream balloon 107 and a distal seal formed by the upstream balloon 105. The portion of the downstream balloon 107 proximal to the distal portion may comprise no pores 126 or may comprise less pores 126 than the distal portion. In some embodiments, distal portion may be defined as a portion of the balloon generally distal to a maximum expanded diameter of the downstream balloon 107. Some of the pores 126 may be configured to be pressed against the blood vessel wall where the proximal fluid seal is formed such that the counter pressure of the blood vessel wall effectively seals those pores 126 from the intravascular environment, as described elsewhere herein. This configuration may prevent or minimize delivery of therapeutic agent into downstream portions of the blood vessel in which the therapeutic agent may be diffused into the bloodstream within the downstream vasculature. In some embodiments, the downstream balloon 107 may be configured to be positioned entirely downstream of the aneurysm creating a sealed volume 142 between the upstream balloon 105 and the downstream balloon 107 which confines the aneurysm.

Figure 3C:
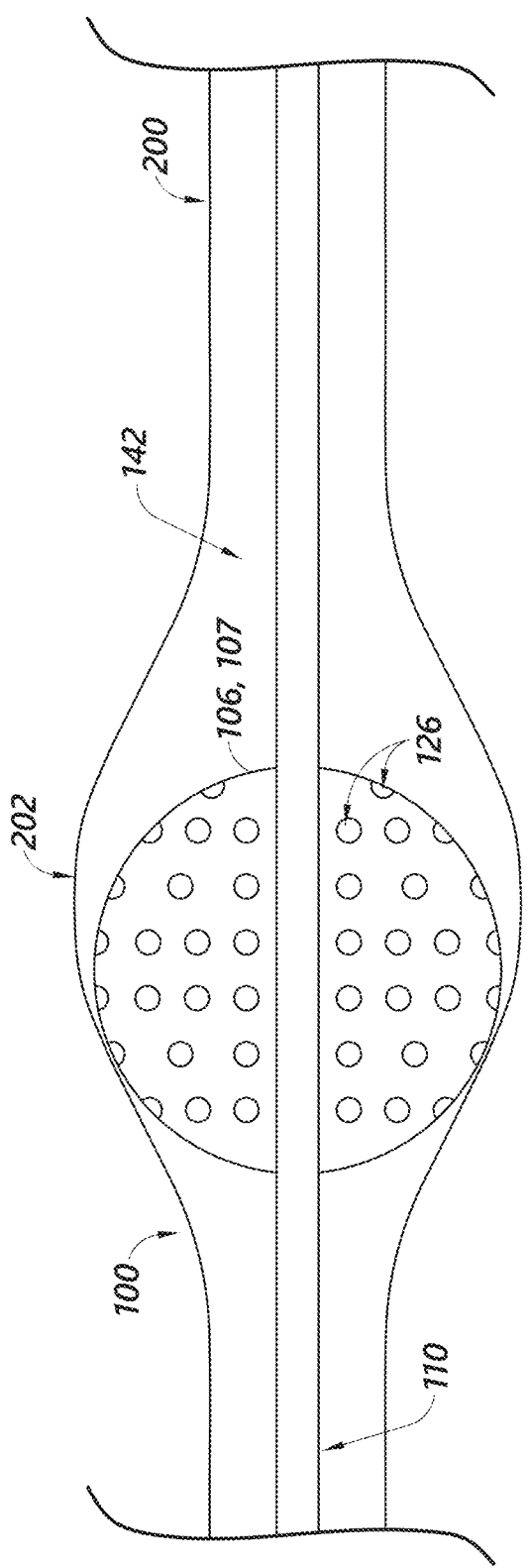

In some embodiments, as schematically illustrated in FIG. 3C, the downstream balloon 107 may comprise a length less than a length of the aneurysm and may be positioned entirely within the aneurysm. The expanded configuration of the downstream balloon 107 may place the expandable membrane of the downstream balloon in contact with or in close proximity to the blood vessel wall of the aneurysm. The delivery catheter 100 may be configured to position the downstream balloon 107 within the aneurysm, such that a midpoint along the length of the balloon 107 is longitudinally aligned substantially with a midpoint of the aneurysm or the midpoint of the balloon 107 may be positioned within a proximal or distal portion of the aneurysm. The downstream balloon 107 may be positioned entirely within the length of the aneurysm or the balloon 107 may be positioned partially within the aneurysm and partially outside the aneurysm. In other embodiments, the upstream balloon 105 may be a weeping balloon in addition to or alternatively to the downstream balloon 107 and comprise some or all of the same or similar features as described with respect to the downstream balloon 107.

In some embodiments, including that shown in FIG. 2A and optionally those shown in FIGS. 2B and 2C, the upstream balloon 105 is connected to the downstream balloon 107 in a fixed spatial relationship, separated by the intermediate shaft segment 120. The length of the intermediate shaft segment 120 may be configured to position the downstream balloon 107 a particular distance downstream from the upstream balloon 105. For example, the upstream balloon 105 may be anchored within the abdominal aorta between the renal arteries. The upstream balloon 105 may occlude antegrade blood flow from the descending aorta and retrograde blood flow from the renal arteries from flowing toward the downstream balloon 107. The length of the intermediate shaft segment 120 may be configured to position the downstream balloon 107 near or adjacent to a typical location of an abdominal aortic aneurysm, as in one of the configurations described with respect to FIGS. 3A-3C. As described elsewhere herein, the delivery catheter 100 may be configured to position the downstream balloon 107 across an aneurysm, if the length of the balloon 107 is substantially the same as or greater than the length of the aneurysm, or near a downstream edge of the aneurysm. In some implementations, the length of the downstream balloon 107 may be less than the length of the aneurysm. In some implementations, the size (for example, length) and/or positioning of the downstream balloon 107 (for example, the length of the intermediate shaft segment 120) may depend on the size of the aneurysm and/or the stage of the aneurysm progression. The abdominal aortic aneurysm may increase in size (and corresponding length of the blood vessel) over time. A user may select from various configurations of delivery catheters 100 which are configured for aneurysms of different sizes, positions, and/or stages of progression.

In some embodiments, the separation distance of the upstream balloon 105 and the downstream balloon 107 may be adjustable. For example, in the embodiments illustrated in FIGS. 2B and 2C, the secondary shaft 114 may optionally be freely translatable within the main shaft 110 along the longitudinal axis of the delivery catheter 100 such that the distance between the upstream balloon 105 and the downstream balloon 107 is variable and adjustable (for example, continuously or incrementally). The distal end of the main shaft 110 may comprise a sealing feature positioned between an internal diameter of the main shaft 110 and an outer diameter of the secondary shaft 114, which allows the secondary shaft 114 to axially translate (for example, slide)

relative to the main shaft 110 while preventing or mitigating fluid flow from the intravascular environment into the first inflation lumen 112. The relative positioning of the main shaft 110 and the secondary shaft 114 may be transiently locked in place by a locking mechanism disposed at the proximal end of the delivery catheter 100. In some embodiments, the secondary shaft 114 may be prevented from advancing distally beyond a distal threshold relative to the main shaft 110 and/or from being retracted proximally beyond a proximal threshold relative to the main shaft 110. For instance, in some embodiments, the upstream balloon 105 may not be configured to be proximally withdrawn past the distal end of the main shaft 110. The upstream balloon 105 may not be configured (for example, dimensioned) to be received within the first central lumen 112. In some embodiments, features at the proximal end of the delivery catheter 100 and/or within the first central lumen 112 between the inner diameter of the main shaft 110 and the outer diameter of the secondary shaft 114 (for example, mechanical catches or latches) may prevent axial translation in the proximal and/or distal direction beyond a certain point.

In some embodiments, the secondary shaft 114 may be removable from the first central lumen 112 of the main shaft 110. The secondary shaft 114 may be reversibly insertable into and removable from the main shaft 110. The secondary shaft 114 may be configured to be removed only when the upstream balloon 105 is in an unexpanded or compressed configuration. In some implementations, the secondary shaft 114 may be inserted into the main shaft 110 and advanced distally beyond the distal end of the main shaft 110 after the main shaft 110 has been navigated to the target site or general target area of the vasculature. In some implementations, the main shaft 110 may be advanced over the secondary shaft 114 after the secondary shaft 114 has been navigated to the target site or general target area of the vasculature. The delivery catheter 100 may be removed from the vasculature after the therapeutic procedure as a single unit or the main shaft 110 or secondary shaft may be removed sequentially in any order. The expandable members 104, 106 may be compressed or unexpanded (for example, the balloons 105, 107 may be deflated) prior to removal of the delivery device 100 or its constituent components from the vasculature.

In some embodiments, one or more of the components of the delivery catheter 100 may comprise radiopaque materials or radiopaque elements (for example, radiopaque rings) may be added to the delivery catheter 100. For example, radiopaque rings may be added to one or more of the distal end of the main shaft 110, the distal end of the secondary shaft 114, the distal and/or proximal ends of the intermediate shaft segment 120, and the upstream or downstream balloons 105, 107 (for example, at proximal and distal ends of the balloons). Use of radiopaque elements or other detectable elements may allow for visual tracking of the delivery catheter within the vasculature, such as through radioscopy or other suitable imaging means, and/or may allow for evaluation of the positioning of the upstream balloon 105 and/or the downstream balloon 107 within the vasculature. In some implementations, the inflation fluid of one or both of the upstream balloon 105 and downstream balloon 107 may include a contrast agent. Use of the contrast agent may allow the user to evaluate the state or amount of inflation of the balloon, may allow the user to determine if the balloon has occluded the blood vessel, and/or, in the case of the downstream balloon 107, may allow the user to monitor the delivery of the therapeutic agent into the blood vessel and/or aneurysm.

In some embodiments, the delivery catheter 100 may be useable with one or more guidewires for facilitating the introduction and/or navigation of the device into and within the vasculature. In some embodiments, a guidewire may be received within the first central lumen 112, such as when the secondary shaft 114 is removable from the first central lumen 112, and/or a guidewire may be received within the secondary central lumen 116. In some embodiments, the lumen, such as the secondary central lumen 116, may be configured to prevent a guidewire from extending distally beyond a certain point along the length of the lumen. For example, the secondary lumen may be dimensioned with a catch or a tapered or step-down in diameter that prevents the guidewire from extending distally any further. The secondary central lumen 116 may be open or closed at a distal end of the secondary shaft 114. The guidewire may be configured to extend distally beyond the distal end of the secondary shaft 114 in embodiments where the central lumen is open distally to the intravascular environment. In some implementations, the delivery catheter 100 may be introduced over the guidewire after the guidewire has been navigated to or near the target site. In some implementations, the delivery catheter 100 may be capable of being navigated to the target site without use of a guidewire. For example, for applications within the abdominal aorta, the delivery catheter 100 may be readily pushed into position via access through the femoral artery without the need for steerability. In some embodiments, the delivery catheter 100 may comprise steerable components, such as the main shaft 110, which may be configured to bend near a distal end 102 of the device. The delivery catheter 100 may comprise one or more pull wires which extend from or from near a distal end 102 of the device to a proximal end of the device. Operation of a control on the proximal end of the delivery catheter 100 may be configured to bend a distal portion of the delivery catheter 100 in one or more directions. Steerability of the delivery catheter 100 may facilitate the introduction and/or navigation of the delivery catheter 100.

In some embodiments, such as that depicted in FIG. 2C, the distal end of the secondary central lumen 116 may be open to the intravascular environment. In some embodiments, the distal end of the main internal lumen 112 may be open, at least partially, to the intravascular environment. In these embodiments, some blood may flow proximally through these lumens across the delivery catheter device. The delivery catheter 100 may be configured such that blood flow through these lumens does not enter the sealed volume 142 between the expanded upstream balloon 105 and expanded downstream balloon 107, as described elsewhere herein. In some embodiments, the blood flow through the internal lumens of the delivery catheter 100 may be in fluid communication with a proximal end of the delivery catheter 100. In some embodiments, the delivery catheter 100 may comprise one or more ports (not shown) in fluid communication with the intravascular environment, positioned proximally to the downstream balloon 107, such that the blood flow, or at least a portion thereof, may be returned to blood vessel downstream of the sealed volume 142. The first central lumen 112 and/or the secondary central lumen 116 may be sealed at a proximal end during use to promote blood flow into the downstream intravascular space rather than through the proximal end of the delivery catheter 100. In some implementations, blood flow through these lumens may be negligible. For instance, the diameter of the lumens may be small enough such that significant volumes of blood are not driven through the lumens during use of the delivery catheter 100. In some implementations, blood flow through these lumens may be non-negligible. In some embodiments, the lumens may be used to maintain blood flow through the aorta during the procedure and may facilitate prolonging the duration of blood occlusion and the therapeutic treatment.

In some embodiments, the lumens described elsewhere herein may not be formed from the concentric positioning of two or more shafts, but rather may be configured as internal lumens formed as channels within the bodies of one or more unitary shafts. For example, the main shaft 110 may extend from a proximal end of the device, through a center of the downstream balloon 107, to the upstream balloon 105. The main shaft 110 may comprise a plurality of internal lumens (for example, non-concentric lumens) formed within the body material of the main shaft 110. The internal lumens may run substantially parallel to one another. The internal lumens may extend to different lengths along the longitudinal axis of the delivery catheter 100. The internal lumens may be in fluid communication with different components of the delivery catheter 100. For example, one internal lumen may be in fluid communication with the upstream balloon 105 and another internal lumen may be in fluid communication with the downstream balloon 107. The main shaft 110 or other shaft components may comprise additional lumens beyond what is described elsewhere herein. For example, the delivery catheter 100 may have lumens configured for receiving guidewires and/or lumens configured for providing aspiration.

For instance, in some embodiments, the delivery catheter 100 may comprise an aspiration lumen in fluid communication with an aspiration port positioned along the intermediate shaft segment 120. FIG. 2B schematically depicts a supplemental internal lumen 138 in fluid communication with a supplemental fluid port 139 disposed on the intermediate shaft segment 120. The supplemental internal lumen 138 may be used as an aspiration lumen or as a drug delivery lumen, as described elsewhere herein. In some implementations, the aspiration lumen may be used to aspirate the intravascular environment within a sealed volume between the upstream balloon 105 and the downstream balloon 107. Aspiration of fluid (for example, blood) from the sealed volume before and/or during delivery of the therapeutic agent may increase the volume and/or concentration of therapeutic agent that may be delivered to the sealed volume using the delivery device 100. In some implementations, the sealed volume 142 may be aspirated after treatment using the therapeutic agent and before the upstream balloon 105 and/or the downstream balloon 107 is deflated. Removal of the therapeutic agent from the intravascular environment prior to restoring blood flow may eliminate, reduce, or mitigate any downstream and/or non-localized effects of releasing the therapeutic agent into the blood stream. In some embodiments, the supplemental internal lumen 138 in fluid communication with the sealed volume 142 may be used to deliver the therapeutic agent into the sealed volume 142 in addition to or alternatively to a weeping balloon.

Figure 4B:
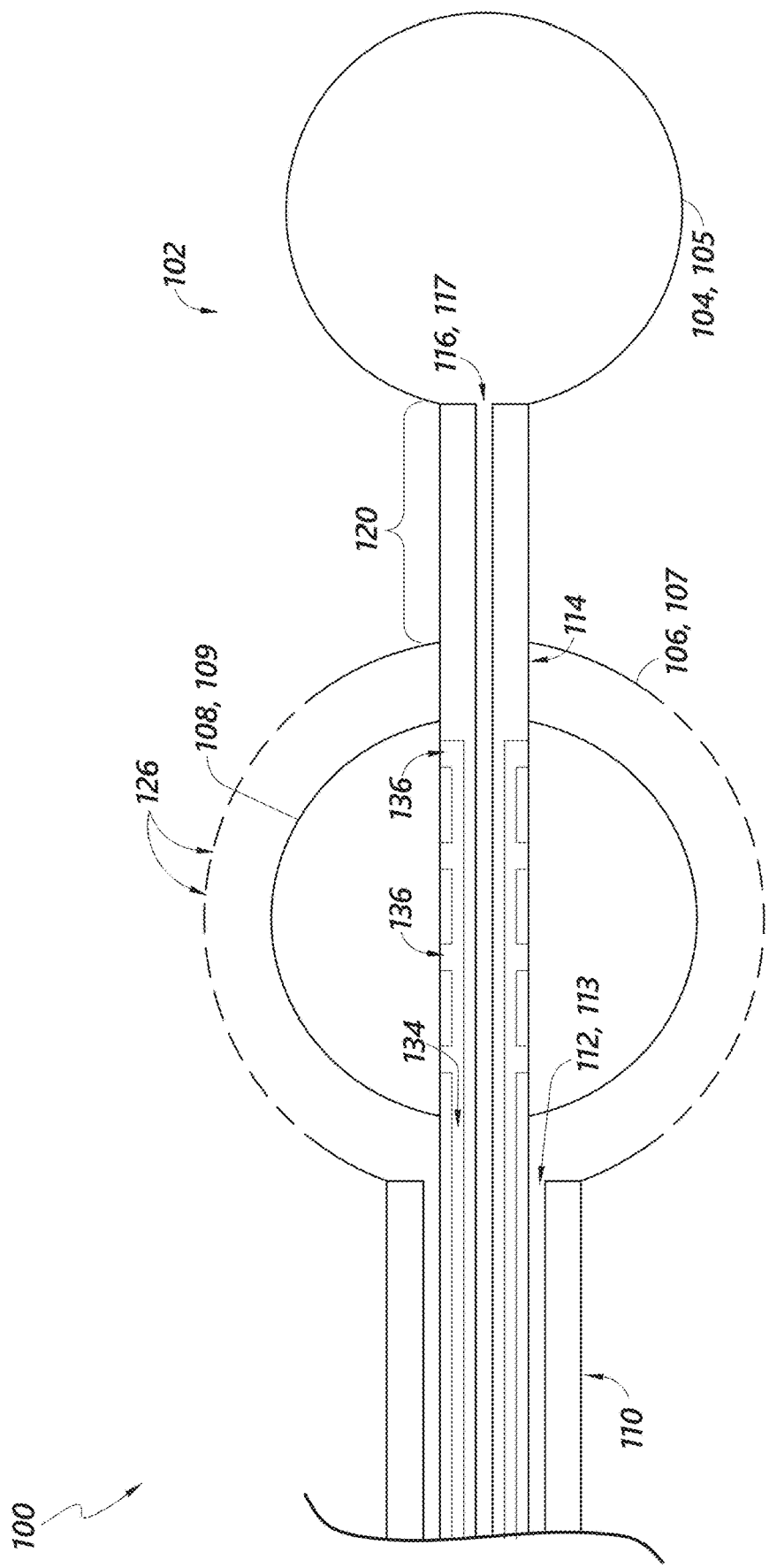
Figure 4C:
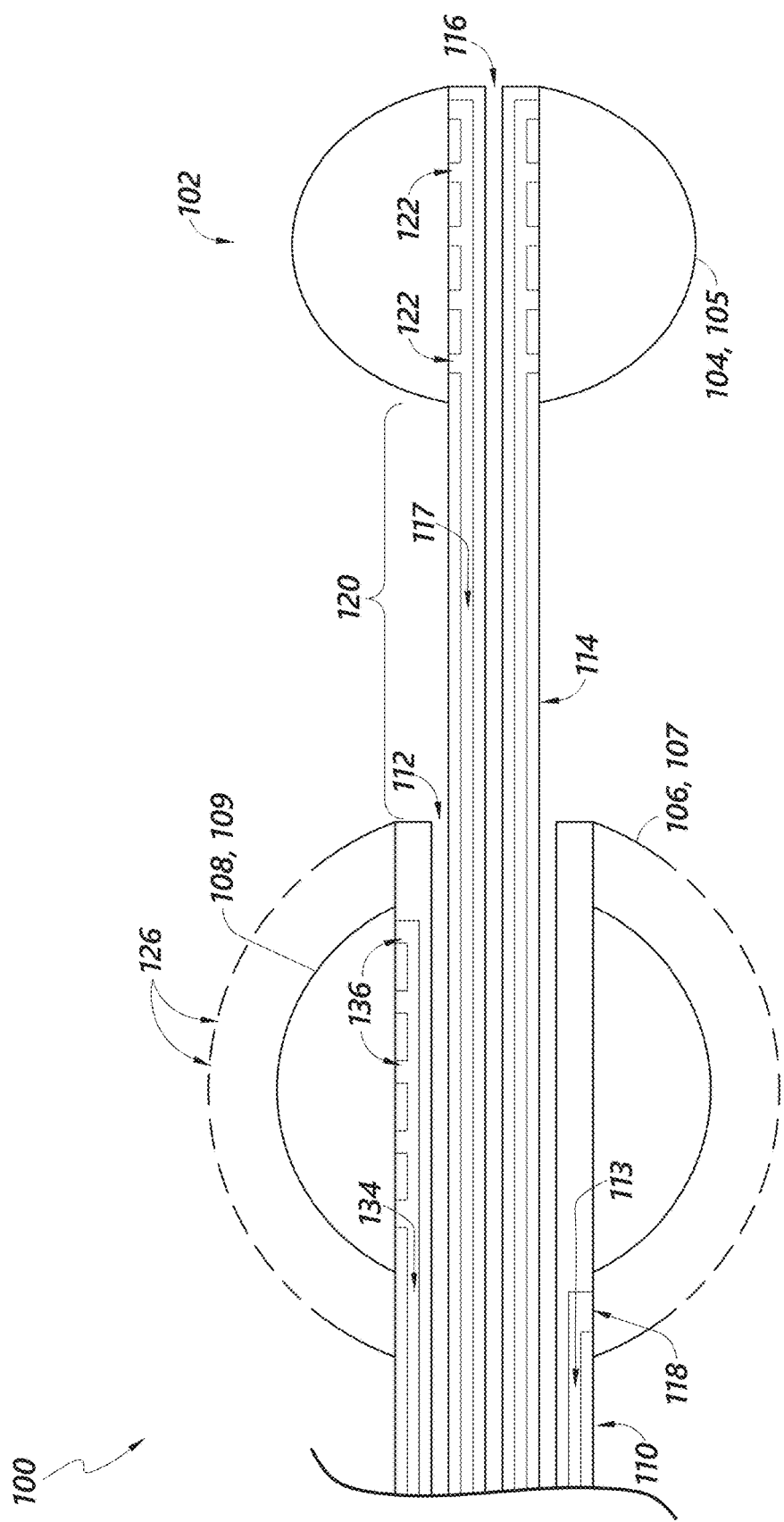

FIGS. 4A-4C schematically illustrates examples of a delivery catheter 100 comprising a third expandable member 108. The third expandable member 108 may be an inner balloon 109 as shown in FIG. 4A. FIGS. 4A and 4B may comprise features that are the same or relatively similar to those described with respect to FIG. 2A, and FIG. 4B may comprise features that are the same or relatively similar to those described with respect to FIG. 2C, except for the inclusion of the inner balloon 109. The inner balloon 109 may be positioned entirely within the interior of the downstream balloon 105 as shown in FIGS. 4A-4C. The inner balloon 109 may be in fluid communication with a tertiary inflation lumen 134. As shown in FIG. 4A, the tertiary inflation lumen 134 may be formed within the main shaft 110. In some embodiments, the tertiary inflation lumen 134 may be formed radially inside the first inflation lumen 113. The tertiary inflation lumen 134, may be formed by the first central lumen 112, as shown in FIG. 4A. In some embodiments, the tertiary inflation lumen 134 may be formed from a separate tubular component that is carried within the first central lumen 112 of the main shaft 110.

The inner balloon 109 may comprise an expandable membrane. The expandable membrane of the inner balloon 109 may comprise the same and/or different material(s) as the expandable membrane of the downstream balloon 107 and/or the upstream balloon 105. In some embodiments, such as that shown in FIG. 4A, the expandable membrane is coupled to (for example, at or near) the secondary shaft 114 forming a fluid tight seal with the secondary shaft 114 such that an interior volume of the inner balloon 109 may be pressurized. Introduction of inflation fluid into the upstream balloon 105 may cause the inner balloon 109 to expand radially outward between the tertiary inflation lumen 134 and the distal fluid tight seal. The distal end of the expandable membrane of the inner balloon 109 may be substantially longitudinally aligned with the distal end of the expandable membrane of the downstream balloon 107 or may be coupled to the secondary shaft 114 at a point proximal to that where the expandable membrane of the downstream balloon 107 is coupled to the secondary shaft 114.

In some embodiments, as shown in FIG. 4B, proximal and distal ends of the expandable membrane of the inner balloon 109 may be coupled to the secondary shaft 114 to form fluid-tight seals around the outer diameter of the secondary shaft 114. The distal end of the expandable membrane of the inner balloon 109 may be substantially longitudinally aligned with the distal end of the expandable membrane of the downstream balloon 107 or may be coupled to the secondary shaft 114 at a point proximal to that where the expandable membrane of the downstream balloon 107 is coupled to the secondary shaft 114. The proximal end of the expandable membrane of the inner balloon 109 may be substantially longitudinally aligned with the proximal end of the expandable membrane of the downstream balloon 107 or may be coupled to the secondary shaft 114 at a point distal to the proximal end of the downstream balloon 109. Inflation fluid may be introduced to pressurize the interior volume of the inner balloon 109 allowing the expandable membrane to expand radially outward between the proximal and distal ends of the expandable membrane of the inner balloon 109 upon the introduction of the inflation fluid. Inflation fluid may be introduced into the interior of the inner balloon 109 through one or more tertiary inflation ports 136 formed in the sidewall of the secondary shaft 114. The tertiary inflation lumen 134 may be disposed within the secondary shaft 114 rather than the main shaft 110. The tertiary inflation ports 136 may pass through a sidewall of the secondary shaft 114. In some embodiments, a plurality of tertiary inflation ports 136 may be spaced longitudinally along the secondary shaft 114 between the proximal and distal ends of the expandable membrane of the inner balloon 109. In some embodiments, a plurality of tertiary inflation ports 136 may be spaced radially around the outer diameter of the secondary shaft 114.

In some embodiments, as shown in FIG. 4C, the tertiary inflation ports 136 are formed in a sidewall of the main shaft 110 and the inner balloon 109 may be coupled at proximal and distal sealing points to an outer diameter of the main shaft 110. In some embodiments, the inner balloon 109 may be a generally toroidal balloon, as described elsewhere herein with respect to downstream balloon 107. The toroidal inner balloon 109 may be disposed within the interior volume of the downstream balloon 107. In some embodiments, the inner surface of the expandable membrane of the toroidal inner balloon 109 may be coupled at a proximal end, distal end, or along a length or portions of the length of the inner surface to the main shaft 110 or secondary shaft 114, depending on the configuration of the delivery catheter 100. In some embodiments, the inner toroidal balloon 109 may be coupled to the expandable membrane of the downstream balloon 107. In some embodiments, the inner toroidal balloon 109 may be coupled to a shaft and the expandable membrane of the downstream balloon 107. In some embodiments, the toroidal inner balloon 109 may be free-floating within the interior volume of the downstream balloon 107. In some embodiments, the downstream balloon 107 may be a generally toroidal balloon as described elsewhere herein and the inner balloon 109 may be disposed within the annular interior volume of the downstream balloon 107. The generally toroidal inner balloon 109 may be coupled to an inner surface and/or an outer surface of the expandable membrane of the generally toroidal downstream balloon 107 or the inner balloon 109 may be free-floating within the annular interior volume of the downstream balloon 107.

The inner balloon 109 may facilitate the expansion of the downstream balloon 107 and/or the expulsion of inflation fluid (including therapeutic agent) from the downstream balloon 107. The inclusion and inflation of an inner balloon 109 may advantageously reduce the volume of inflation fluid within the downstream balloon 107 necessary to expand the downstream balloon and/or expel inflation fluid through the pores 126 of the downstream balloon 107. The reduction of inflation fluid used within the downstream balloon 109 may conserve the therapeutic agent. The use of the inner balloon 109 may reduce the pressure within the interior of the downstream balloon 107 at which inflation fluid is expelled through the pores 126. In some implementations, a volume of inflation fluid may be introduced into the interior volume of the downstream balloon 107 which is insufficient to fully expand the downstream balloon 107 or to expand the downstream balloon 107 to the inner diameter of the target blood vessel. The inner balloon 109 may be inflated, pressing the volume of inflation fluid within the interior of the downstream balloon 107 against the expandable membrane of the downstream balloon 107 and causing the downstream balloon 107 to expand. In some embodiments, the volume of inflation fluid may be delivered through the pores 126 at a substantial (for example, non-negligible) rate as soon as the combined volume of the inner balloon 109 and the volume of inflation fluid within the downstream balloon 107 is substantially equal to the interior volume of the downstream balloon 107 or as soon as the reduction of volume available for the volume of inflation fluid is small enough that it causes the internal pressure within the downstream balloon 107 to surpass a minimum threshold.

Any or all of the balloons described herein may comprise various shapes. The shapes of the device balloons may be the same or different. In various embodiments, the shape of the balloon may be defined by a surface of revolution. In some embodiments, the balloons may comprise a substantially spherical shape. In some embodiments, the balloons may comprise a prolate spheroid shape, such as a prolate spheroid shape or an oblate spheroid shape. The longitudinal axis of the spheroid may be aligned with the longitudinal axis of the delivery catheter 100. In various embodiments, the length of the balloon may be larger than a diameter of the balloon in its expanded configuration (for example, a prolate spheroid). In some embodiments, the balloons may comprise a pointed football shape. In some embodiments, the balloons may comprise a cylindrical shape. The balloons may comprise distinct proximal and distal surfaces extending from the longitudinal axis of the delivery device 100 to form an edge with an outer surface of the balloon. The proximal and/or distal surfaces may be substantially flat, generally concave, and/or generally convex. The outer surface of the balloons may extend to a diameter greater than, substantially equal to, or less than a diameter of the proximal surface and/or the distal surface. The outer surface may be generally flat, concave, or convex. In some embodiments the pores 126 of the weeping balloon may be only disposed on the outer surface of the balloon or on an outer surface and only one of the proximal and distal surfaces (for example, the distal surface of the downstream balloon 107). In some embodiments, the downstream balloon 107 may comprise one or more inner layers including inner pores. In some embodiments, the inner pores may generally comprise diameters greater than or equal to the diameter of the pores 126. The inner pores may serve as baffles which may help facilitate uniform distribution of the inflation fluid (and therapeutic agent) within the interior of the downstream balloon 107.

The outer diameter of the upstream balloon 105 in an expanded configuration (for example, at its widest point) may be at least approximately 1.5 cm, 1.75 cm, 2.0 cm, 2.25 cm, 2.5 cm, 3.0 cm, or 3.5 cm. The outer diameter of the upstream balloon 105 in an expanded configuration may be configured to match or slightly exceed the diameter of a healthy abdominal aorta (for example, near the renal arteries). In some embodiments, the downstream balloon 107 may be configured to expand to the diameter of a health aorta or slightly exceed the diameter of a healthy aorta such that it may form a fluid seal with the aorta downstream of and optionally upstream of an abdominal aortic aneurysm or with a relatively non-enlarged portion or portions of the aneurysm (for example, near the proximal and/or distal edges of the aneurysm). In such embodiments, the outer diameter of the downstream balloon 107 in an expanded configuration may be substantially equal to the outer diameter of the upstream balloon 105 or slightly larger than the outer diameter of the upstream balloon 105 in an expanded configuration. The outer diameter of the downstream balloon 107 in an expanded configuration may be at least approximately 1.5 cm, 1.75 cm, 2.0 cm, 2.25 cm, 2.5 cm, 3.0 cm, 3.5 cm, or 4.0 cm. In embodiments, where the downstream balloon 107 is configured to be expanded well into the sac of the abdominal aortic aneurysm, the downstream balloon 107 may have an outer diameter in the expanded configuration substantially larger than that of the upstream balloon 105. The outer diameter of the downstream balloon 107 in an expanded configuration may be at least approximately 1.5 cm, 1.75 cm, 2.0 cm, 2.25 cm, 2.5 cm, 3.0 cm, 3.5 cm, or 4.0 cm, 4.5 cm, 5.0 cm, 5.5 cm, 6.0 cm, 6.5 cm, 7.0 cm, 7.5 cm, or 8.0 cm. In some embodiments, the expanded diameter of the downstream balloon 107 may be at least about 100%, 125%, 150%, 175%, 200%, 300%, 400%, or 500% the expanded diameter of the upstream balloon 105. In some embodiments, the total volume of the downstream balloon 107 (for example, in an expanded configuration) or of the holding capacity of deliverable fluid of the delivery catheter 100 (for example, the interior volume of the downstream balloon 107 and the first inflation lumen 113) may be at least about 1 mL, 2 mL, 3 mL, 5 mL, 10 mL, 20 mL, 30 mL, 40 mL, 50 mL, 60 mL, 70 mL, 80 mL, 90 mL, 100 mL, 125 mL, 150 mL, 175 mL, or 200 mL.

Delivery catheters 100 in which the downstream balloon 107 expands into or is pressed into contact with the abdominal aortic aneurysm may be particularly suited for aneurysms that are less prone to rupture. In some instances, the risk of rupture may be characterized by the size (for example, maximal diameter) of the aneurysm. Smaller aneurysms (for example, no greater than about 6 cm, 5 cm, 4 cm, or 3 cm) may be less prone to rupture. Abdominal aortic aneurysms may tend to grow in size over time and become more prone to rupture. The blood vessel wall of the aneurysm may weaken as the aneurysm grows. In some implementations, the delivery catheters 100 described herein, may be particularly useful for early interventional treatment of diagnosed abdominal aortic aneurysms.

The length of the downstream balloon 107 may be at least about 0.5 cm, 1 cm, 2 cm, 3 cm, 4 cm, 5 cm, 6 cm, 7 cm, 8 cm, 9 cm, or 10 cm. In some embodiments, the length of the downstream balloon 107 may be configured to span the length of the abdominal aortic aneurysm, as described elsewhere herein. In some embodiments, the abdominal aortic aneurysm may be relatively small or in an early-stage of development. In some embodiments, the length of the upstream balloon 105 may be the same as the length of the downstream balloon 107 or it may be shorter than the length of the downstream balloon 107. In some embodiments, the length of the upstream balloon 105 may be at least about 0.5 cm, 1 cm, 1.5 cm, 2 cm, 2.5 cm, or 3 cm. In some embodiments, the upstream balloon 105 may comprise a generally spherical shape and the downstream balloon 107 may comprise a generally prolate spheroid shape.

In embodiments comprising an inner balloon 109, the inner balloon 109 may be the same or a different shape as the downstream balloon 107. The inner balloon 109 may comprise an expanded diameter the same as or less than that of the downstream balloon 107. The inner balloon 109 may comprise a length the same as or less than that of the downstream balloon 105. The inner balloon 109 may comprise a maximum interior volume the same as or less than that of the downstream balloon 105. In some embodiments, the volume, length, and/or expanded diameter of the inner balloon 109 may be no less than approximately 100%, 95%, 90%, 85%, 80%, 75%, 70%, 65%, 60%, 55%, 50%, 45%, or 40% of the downstream balloon 107. In embodiments, in which the length of the inner balloon 109 is less than the length of the downstream balloon 107, the inner balloon 109 may be positioned, with respect to the longitudinal axis, centrally within the downstream balloon, or toward the proximal or distal end of the downstream balloon 107. The proximal end of the inner balloon 109 may or may not be aligned with the proximal end of the downstream balloon 107. The distal end of the inner balloon 109 may or may not be aligned with the distal end of the downstream balloon 107.

In some embodiments, the unexpanded diameters of the upstream balloon 105, downstream balloon 107, and/or the inner balloon 109 of the delivery catheter 100 may be no greater than about 0.5 mm, 1 mm, 2 mm, 3 mm, 4 mm, 5 mm, 6 mm, 7 mm, 8 mm, 9 mm, or 10 mm. The unexpanded diameter of one or more of the balloons may be configured to be received within the lumen of a concentrically surrounding shaft or access sheath.

In some embodiments the weeping balloon (for example, downstream balloon 107) may comprise at least 5, 10, 20, 30, 40, 50,100,200, 300, 500, or 1000 pores 126. The diameter (or longest dimension) of the individual pores 126 may be the same or may be different. The diameter of the pores 126 (for example, in an expanded configuration) may be no greater than approximately 0.01 mm, 0.02 mm, 0.03 mm, 0.05 mm, 0.04 mm, 0.05 mm, 0.06 mm, 0.07 mm, 0.08 mm, 0.09 mm, 0.1 mm, 0.2 mm, 0.3 mm, 0.4 mm, 0.5 mm, 0.6 mm, 0.7 mm, 0.8 mm, 0.9 mm, or 1 mm. In some embodiments, the diameter of the pores 126 in the expanded configuration may be at least about 1×, 1.25×, 1.5×, 1.75×, 2×, 3×, 4×, 5×, or 10×, the diameter of the pores 126 in the unexpanded configuration. The pores 126 may be the same size regardless the state of expansion in some embodiments, particularly if downstream balloon 107 comprises a non-compliant expandable membrane. In some embodiments, the pores 126 may be disposed over an entire length of the downstream balloon 107. In some embodiments, the pores 126 may be disposed over only about the middle 20%, 30%, 40%, 50%, 60%, 70%, 80%, 90% or 95% of the length of the downstream balloon 107 (for example, in an expanded configuration). In some embodiments, the pores 126 may be disposed only over a distal portion of the length of the downstream balloon 107, the distal portion comprising no more than about 20%, 30%, 40%, 50%, 60%, 70%, 80%, 90% or 95% of the length of the downstream balloon 107 (for example, in an expanded configuration).

In some embodiments, the outer diameter of the main shaft 110 may be no greater than about 1 mm, 2 mm, 3 mm, 4 mm, 5 mm, 6 mm, 7 mm, 8 mm, 9 mm, or 10 mm. In some embodiments, the outer diameter of the main shaft 110 may be approximately 9 Fr, 10 Fr, 11 Fr, 12 Fr, 13 Fr, 14 Fr, 15 Fr, 16 Fr 17 Fr, or 18 Fr. The main shaft 110 may have a sidewall thickness of no greater than approximately 0.1 mm, 0.2 mm, 0.3 mm, 0.4 mm, 0.5 mm, 0.6 mm, 0.7 mm, 0.8 mm, 0.9 mm, 1 mm, 1.25 mm, 1.5 mm, 1.75 mm, or 2.0 mm. The secondary shaft 114 may comprise an outer diameter substantially equal to or slightly less than the inner diameter of the main shaft 110. In some embodiments, the length of the delivery catheter 100 from its proximal end to its distal end 102 may be at least about 20 cm, 25 cm, 30 cm, 35 cm, 40 cm, 45 cm, or 50 cm.

The various components of the delivery catheter 100 may be fabricated from one or more materials known in the art of catheter design. The materials, particularly those configured to be placed in contact with the intravascular environment, may be fabricated from biocompatible materials. In some embodiments, one or more components of the delivery catheter, such as the main shaft 110 and/or secondary shaft 114, may comprise polyurethane (PU), polyethylene (PE), polyvinylchloride (PVC), polytetrafluoroethylene (PTFE), polyvinylidene fluoride (PVDF), other fluoropolymers, polyether block amide (for example, PEBAX® or Vestamid®), nylon, etc. In various embodiments, the shafts and/or balloons may be chemically and/or mechanically treated/processed (for example, plasma etched) or coated to provide biocompatibility or mechanical properties (for example, lubricious and/or hydrophilic surface properties). For example, one or more components of the delivery catheter 100 may be coated with a formulation comprising polyethylene glycol (PEG).

In some embodiments, the delivery catheter 100 may comprise a handle at its proximal end. The main shaft 110 of the delivery catheter 100 may extend from a distal end of the handle. The main shaft 110 may continue through the handle and/or be in fluid communication with a channel formed within the handle. The handle may comprise a grip portion for the operator to grasp. The handle may be used to distally advance and/or proximally retract the delivery catheter 100. In embodiments where the delivery catheter 100 is steerable, the handle may comprise one or more controls for steering (for example, bending a distal portion of) the delivery catheter 100, such as by controlling the extension and retraction of one or more pull wires. In some embodiments, the handle may comprise one or more fluid ports in fluid communication with one or more of the internal lumens, such as the first inflation lumen 113 and the secondary inflation lumen 117. The fluid ports may comprise luer-type connectors for connecting to fluid lines, such as for supplying inflation fluid to the delivery catheter 100. In some embodiments, the fluid ports may comprise stopcocks or other valves for regulating fluid flow from a fluid supply source into the handle. The fluid lines may extend to sources of pressurized fluid (for example, inflation fluid) such as a syringe or pump and/or a vacuum source for providing aspiration. In some embodiments, one more fluid ports may be configured to receive a component of the delivery catheter 100. For example, in embodiments, in which the secondary shaft 114 is removable from the main shaft 110, the secondary shaft 114 may be insertable into a proximal end of the handle through the fluid port to be received in the main shaft 110. The secondary shaft 114 may be advanced through the fluid port until it extends distally beyond the main shaft 110. The handle may comprise a means for temporarily fixing the relative positioning of the shafts 110, 114, as described elsewhere herein. Similarly, in some embodiments, a guidewire may be insertable into a proximal end of the handle through one or more fluid ports to be received in the first central lumen 112 or the secondary central lumen 116. In some embodiments, in which inflation fluid is supplied by a pump or mechanized syringe, and/or in which aspiration is provided, there may be a controller for controlling flow rate through the internal lumens. The controller may be remote to the handle or coupled to or integral with the handle. The handle may comprise one or more controls for modulating (for example, increasing, decreasing, stopping, and/or starting) the flow rate of the inflation fluid and/or the vacuum pressure supplied to one or more of the internal lumens. In some embodiments, the controls may be remote from the handle (for example, part of a remote controller).

Delivery Methods

In some implementations, the delivery catheter 100, described elsewhere herein, or a device having similar features to the delivery catheter 100 may be used to therapeutically treat an aneurysm or a target side of a blood vessel by delivering a therapeutic agent to the aneurysm or target site. Described herein is an example of treating an abdominal aortic aneurysm using the delivery catheter 100 to deliver a therapeutic solution comprising PGG. Variations of the procedure described herein may be encompassed. In some implementations, a device different from the delivery catheter 100 may be used. In some implementations, a therapeutic other than or in addition to PGG may be delivered. In some implementations, the therapeutic agent may be delivered to another blood vessel or body lumen other than the aortic artery. In some implementations, the treatment may be applied for another type of aneurysm or for treatment of a blood vessel wall or section of blood vessel that does not comprise an aneurysm, is healthy, suffers from a different diseased condition, and/or the therapeutic agent may be intended to be delivered across the blood vessel wall to target the cellular or extracellular environment adjacent the blood vessel.

A method for treating an abdominal aortic aneurysm is described herein. The method may include or omit any of the steps described elsewhere herein described in relation to the delivery catheter 100. In some embodiments, the delivery catheter 100 is introduced into a femoral artery of the patient. The delivery catheter 100 may be introduced with all expandable members (for example, upstream balloon 105 and downstream balloon 107) in an unexpanded configuration. The delivery catheter 100 may be introduced through an optional access sheath. The distal end 102 of the delivery catheter 100 may be navigated into the abdominal aorta and the upstream balloon 105 positioned at a point upstream of the target abdominal aneurysm. In some embodiments, a guidewire may be navigated to the target location and the delivery catheter 100 may be introduced over the guidewire as described elsewhere herein. In some embodiments, the delivery catheter 100 may be received over a guidewire and navigated to the target location contemporaneously with the guidewire, using the guidewire to steer the distal end 102 of the delivery catheter 100. In some embodiments, the delivery catheter 100 may be introduced without the use of a guidewire. The upstream balloon 105 may be positioned approximately between the renal arteries. The expansion of the upstream balloon 105 partially into the renal arteries may help anchor the balloon. The total procedure time may be sufficiently low (for example, no more than 2-3 min), as described elsewhere herein, such that occlusion of blood flow to the renal arteries may safely be maintained during the procedure. In some embodiments, the upstream balloon 107 may be anchored downstream of the renal arteries. Anchoring within a location downstream of the renal arteries may allow longer operation times during which blood flow is occluded. The upstream balloon 105 may be expanded with the introduction of inflation fluid into the upstream balloon 105. The upstream balloon 105 may be expanded until the delivery catheter 100 is securely anchored in the blood vessel and/or until the blood flow downstream of the upstream balloon 105 has been occluded. In some embodiments, the operation may be performed under indirect visualization, such as radioscopy. A suitable contrast agent for the method of visualization, (for example, radiocontrast media for radioscopy) may be injected into the blood stream prior to and/or during the operation to visualize blood flow. Accordingly, the occlusion of the blood flow may be visually assessed by indirect visualization.

The downstream balloon 107 may be positioned within, downstream of, or along a downstream edge of the abdominal aneurysm. In embodiments in which the length of the intermediate shaft segment 120 is adjustable, the delivery catheter 100 may be adjusted to position the downstream balloon 107 in place after the upstream balloon 105 has been anchored in place. The downstream balloon 107 may be expanded with the introduction of inflation fluid into the upstream balloon 105. The downstream balloon 107 may be expanded until retrograde blood flow from downstream of the downstream balloon 107 is occluded. Injection of a contrast agent into the bloodstream may be used to confirm occlusion of blood flow as described elsewhere herein. The inflation of the upstream balloon 105 and downstream balloon 107 may create a fluidly sealed volume 142 within a section of the blood vessel between the two balloons 105, 107. In some implementations, the downstream balloon 107 may be inflated immediately after inflation of the upstream balloon 105 to prevent or minimize the amount of retrograde blood flow into the sealed volume prior to the complete inflation of the downstream balloon 107. In some embodiments, the upstream balloon 105 and the downstream balloon 107 may each be partially inflated, sequentially or simultaneously, and then the upstream balloon 105 may be further expanded to occlude antegrade flow followed by further expansion of the downstream balloon 107 to occlude retrograde flow. In some embodiments, the downstream balloon 107 may be inflated simultaneously with or prior to the inflation of the upstream balloon 105.

In some embodiments, the delivery catheter 100 may comprise an inner balloon 109 positioned within the downstream balloon 107, as described elsewhere herein. In some embodiments, the inner balloon 109 may be partially or fully expanded before inflation fluid is introduced into the downstream balloon 107. In some embodiments, the downstream balloon 107 may be filled with a volume of inflation fluid prior to or simultaneously with the inflation of the inner balloon 109. The first inflation lumen 113 may be configured at a proximal end to prevent unintended proximal flow of inflation fluid due to expansion of the inner balloon 109. For example, an inflation fluid line may be clamped or a pressure may be maintained on a syringe to prevent fluid flow of inflation fluid proximally from the downstream balloon 107 as the inner balloon 109 is expanded. By preventing or inhibiting proximal flow of inflation fluid, expansion of the inner balloon 109 may better promote the expulsion of the volume of inflation fluid within the downstream balloon 107 through the pores 126. In some embodiments, the inflation fluid in communication with the downstream balloon 107 may be switched over to a solution comprising the therapeutic agent after or during expansion of the downstream balloon 107 or the therapeutic agent may be added into the inflation fluid during or after inflation of the downstream balloon 107, as described elsewhere herein. In some embodiments, the initial volume of inflation fluid introduced into the downstream balloon 107 may comprise the therapeutic agent.

Upon inflation of the downstream balloon 107 or the downstream balloon 107 and the inner balloon 109, the inflation fluid, or a partial volume thereof, within the downstream balloon 107 may be expelled through the pores 126, or a portion of the pores 126, into the intravascular environment. The pores 126 may be positioned on a surface of the expandable membrane of the downstream balloon 127 so as to deliver at least some, if not all or a majority of, the delivered inflation fluid into the sealed volume 142 between the upstream balloon 105 and the downstream balloon 107 or a sub-volume thereof. The sub-volume may be a sealed volume (for example, sealed space 140) formed by the downstream balloon 107 placed in contact with the blood vessel. In embodiments without an inner balloon 109, inflation fluid comprising the therapeutic agent may continue to be supplied to downstream balloon 107 at a pressure or volumetric flow rate configured to maintain the downstream balloon 107 in an expanded configuration after expansion. The delivery device 100 may be configured to provide infusion of the therapeutic agent at a constant pressure. The introduction of therapeutic inflation fluid into the downstream balloon 107 may be maintained long enough to deliver the therapeutic inflation fluid through the pores 126 for a desired duration of time and/or to deliver a predetermined volume of therapeutic inflation fluid through the pores 126. In embodiments comprising an inner balloon 109, the therapeutic inflation fluid may continue to be introduced into the downstream balloon 107 after inflation of the downstream balloon 107 and the inner balloon 109. In some embodiments, the volume of inflation fluid within the downstream balloon 107 may not be replenished as the inner balloon 109 expands to expel the therapeutic inflation fluid through the pores 126.

In some embodiments, the therapeutic agent may be PGG. The PGG may be dissolved in the therapeutic inflation solution at a final concentration that is no less than approximately 0.01%, 0.05%, 0.1%, 0.2%, 0.3%, 0.4%, 0.5%, 0.6%, 0.7%, 0.8%, 0.9%, or 1% (w/v). As described elsewhere herein, higher concentrations of PGG may provide for more effective treatment, especially over shorter treatment times. Accordingly, higher concentrations may allow shorter treatment time. Higher purity PGG may be less toxic, due to absence of toxic impurities, than lower purity PGG. Accordingly, higher purity PGG may be safer to user at higher concentrations than lower purity PGG. The PGG may be dissolved in an inflation fluid such as saline (for example, via a hydrolyzer as described elsewhere herein). The volume of delivered therapeutic inflation fluid may be no more than approximately 150 mL, 125 mL, 100 mL, 75 mL, 50 mL, 40 mL, 30 mL, 20 mL, 15 mL, 10 mL, 8 mL, 5 mL, 3 mL, or 1 mL. In some embodiments, inflation fluid may be delivered through the downstream balloon 107 until a sealed volume, as described elsewhere herein, is filled. In some embodiments, filling of the volume may be detectable by an increase in resistance (a counter pressure) to the delivery of inflation fluid. In some embodiments, filling of the volume may be visually discernable if the inflation fluid comprises a detectable contrast agent. The duration of delivery may be no more than about 30 min, 10 min, 5 min, 4 min, 3 min, 2 min, 1 min, 45 seconds, 30 seconds, 20 seconds, or 10 seconds. The duration of delivery may be shorter in embodiments in which the renal arteries are occluded by the delivery catheter 100. In some implementations, procedures involving aortic occlusions no longer than approximately 10 min may advantageously be performed without the need for general anesthesia. The precise volume of delivered fluid and/or the duration of delivery may depend on the size of the aneurysm or volume of the targeted section of blood vessel to be treated. In some embodiments, the therapeutic inflation solution may be delivered to the downstream balloon 107 at a volumetric flow rate of between approximately 0.05 mL/min and 20 mL/min, 0.1 mL/min and 10 mL/min, 0.5 mL/min and 8 mL/min, or 1 mL/min and 5 mL/min, during the delivery of the therapeutic agent to the blood vessel. In some embodiments, the downstream balloon 107 may be inflated by delivery of inflation fluid at the same volumetric flow rate at which the inflation fluid is introduced during delivery of the therapeutic agent after expansion. In some embodiments, the downstream balloon 107 may be inflated with a volumetric flow rate that is faster than the volumetric flow rate of delivery after expansion. A faster flow rate during expansion of the downstream balloon 105 may facilitate expanding the balloon as the inflation fluid leaks through the pores 126.

By expanding the upstream balloon 107 and occluding downstream blood flow prior to expansion of the downstream balloon 105, the counter pressure needed to cause expansion of the downstream balloon 107 within the intravascular environment may advantageously be reduced. After the downstream blood flow is occluded, the downstream balloon 107 may be expanded upon exceeding the diastolic blood pressure of the patient (for example, approximately 60-80 mmHg), whereas if the downstream blood flow is not occluded, the systolic pressure (for example, approximately 90-120 mmHg) may need to be exceeded. Thus, occluding the downstream blood flow prior to expansion (or full expansion) of the downstream blood flow may facilitate expansion of a weeping balloon, in which pressure may be continually released, such as downstream balloon 107.

In some embodiments, the blood vessel, or a portion thereof (for example, the sealed volume 142 between the upstream balloon 105 and the downstream balloon 107) may be rinsed prior to or after delivery of the therapeutic agent. A rinsing solution (for example, saline) may be introduced to the intravascular space through the downstream balloon 107 prior to delivery (for example, during expansion as described elsewhere herein) or after delivery of the therapeutic agent. In some embodiments, a rinsing solution may be introduced through a separate internal lumen as described elsewhere herein. For example, a rinsing solution may be introduced into the sealed volume through a fluid port positioned along the intermediate shaft segment 120.

In some embodiments, fluid within the blood vessel, or a portion thereof (for example, the sealed volume 142 between the upstream balloon 105 and the downstream balloon 107), may be aspirated through the delivery catheter 100. For example, aspiration may be provided through a separate internal lumen through an aspiration port positioned along the intermediate shaft segment 120, as described elsewhere herein. In some embodiments, the sealed volume 142 may be aspirated to remove any blood and/or rinsing solution prior to delivery of the therapeutic agent. In some embodiments, the sealed volume 142 may be rinsed contemporaneously (for example, continuously or intermittently) with the delivery of the therapeutic agent, such that fresh volumes of the therapeutic inflation fluid are introduced into the intravascular space. In some embodiments, the sealed volume 142 may be aspirated to remove the therapeutic agent and/or rinsing solution prior to deflating the upstream balloon 105 and/or downstream balloon 107. Aspiration may advantageously prevent non-targeted delivery of the therapeutic agent to other parts of the blood vessel or body by releasing the therapeutic agent into the blood stream upon deflation of the balloons 105, 107.

Upon completion of the therapeutic treatment the expandable members 104, 106 may be compressed or de-expanded for removal of the delivery catheter 100 from the vasculature. The upstream balloon 105 and downstream balloon 107, and/or the inner balloon 109 may be deflated by withdrawing the inflation fluid proximally through the first inflation lumen 113 and secondary inflation lumen 117, respectively. In some embodiments, the downstream balloon 107 may be deflated, or at least partially deflated, by forcing all or a portion of the inflation fluid through the pores 126 of the expandable membrane without replenishing the inflation fluid within the downstream balloon 107. The upstream balloon 105 may be deflated prior to, after, or substantially simultaneously with the deflation of the downstream balloon 107. The inner balloon 109, when present, may be deflated prior to or substantially simultaneously with the downstream balloon 107. Upon deflation of the balloons, blood flow may be restored to portions of the aorta downstream of each balloon. The total duration of time for which blood flow is occluded may be no greater than about 30 min, 10 min, 5 min, 4 min, 3 min, 2 min, 1 min, 45 seconds, 30 seconds, 20 seconds, or 10 seconds.

The delivery catheter 100 may be removed from the body by withdrawing the delivery catheter 100 proximally through the vascular access point. In some embodiments in which the delivery catheter 100 comprises multiple components (for example, main shaft 110 and secondary shaft 114 are separable) or is used in conjunction with ancillary components (for example, an access sheath and/or guidewire), the components may be withdrawn in a reverse order in which they were introduced, the components may be withdrawn in a different order, and/or the components or subgroups thereof may be withdrawn contemporaneously. In some embodiments, one or both of the expandable members 104, 106 may need to be placed into an unexpanded configuration or at least partially de-expanded in order to withdraw the delivery catheter 100.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

The term "Solvate" as used herein is a broad term, and is to be given its ordinary and customary meaning to a person of ordinary skill in the art (and is not to be limited to a special or customized meaning), and refers without limitation to the compound formed by the interaction of a solvent and a compound described herein or salt thereof. Suitable solvates are pharmaceutically acceptable solvates including hydrates.

The term "pharmaceutically acceptable salt" as used herein is a broad term, and is to be given its ordinary and customary meaning to a person of ordinary skill in the art (and is not to be limited to a special or customized meaning), and refers without limitation to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $(CH_3)_2CHCH_2$—$CH_3CH_2CH(CH_3)$— and $(CH_3)_3C$—.

The term "halogen" or "halo," as used herein, is a broad term, and is to be given its ordinary and customary meaning to a person of ordinary skill in the art (and is not to be limited to a special or customized meaning), and refers without limitation to any one of the radio-stable atoms of column 7 of the Periodic Table of the Elements, for example, fluorine, chlorine, bromine, or iodine.

As used herein, "alkyl" is a broad term, and is to be given its ordinary and customary meaning to a person of ordinary skill in the art (and is not to be limited to a special or customized meaning), and refers without limitation to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; for example, "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "haloalkyl" is a broad term, and is to be given its ordinary and customary meaning to a person of ordinary skill in the art (and is not to be limited to a special or customized meaning), and refers without limitation to the alkyl moiety substituted with at least one halo group. Examples of haloalkyl groups include, but are not limited to, —$CF_3$, —$CHF_2$, —$CH_2F$, —$CH_2CF_3$, —$CH_2CHF_2$, —$CH_2CH_2F$, —$CH_2CH_2Cl$, or —$CH_2CF_2CF_3$.

As used herein, "alkoxy" is a broad term, and is to be given its ordinary and customary meaning to a person of ordinary skill in the art (and is not to be limited to a special or customized meaning), and refers without limitation to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" is a broad term, and is to be given its ordinary and customary meaning to a person of ordinary skill in the art (and is not to be limited to a special or customized meaning), and refers without limitation to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" is a broad term, and is to be given its ordinary and customary meaning to a person of ordinary skill in the art (and is not to be limited to a special or customized meaning), and refers without limitation to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methylpropen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" is a broad term, and is to be given its ordinary and customary meaning to a person of ordinary skill in the art (and is not to be limited to a special or customized meaning), and refers without limitation to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

The term "aromatic" as used herein is a broad term, and is to be given its ordinary and customary meaning to a person of ordinary skill in the art (and is not to be limited to a special or customized meaning), and refers without limitation to a ring or ring system having a conjugated pi electron system and includes both carbocyclic aromatic (for example, phenyl) and heterocyclic aromatic groups (for example, pyridine). The term includes monocyclic or fused-ring polycyclic (i.e., rings which share adjacent pairs of atoms) groups provided that the entire ring system is aromatic.

As used herein, "aryl" is a broad term, and is to be given its ordinary and customary meaning to a person of ordinary skill in the art (and is not to be limited to a special or customized meaning), and refers without limitation to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" are broad terms, and are to be given their ordinary and customary meaning to a person of ordinary skill in the art (and are not to be limited to a special or customized meaning), and refer without limitation to RO— and RS—, in which R is an aryl as is defined above, such as "$C_{6-10}$ aryloxy" or "$C_{6-10}$ arylthio" and the like, including but not limited to phenyloxy.

As used herein, "aralkyl" or "arylalkyl" are broad terms, and are to be given their ordinary and customary meaning to a person of ordinary skill in the art (and are not to be limited to a special or customized meaning), and refer without limitation to an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "alkylene" is a broad term, and is to be given its ordinary and customary meaning to a person of ordinary skill in the art (and is not to be limited to a special or customized meaning), and refers without limitation to a branched, or straight chain fully saturated di-radical chemical group containing only carbon and hydrogen that is attached to the rest of the molecule via two points of attachment (i.e., an alkanediyl). The alkylene group may have 1 to 20 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$ alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene.

As used herein, "heteroaryl" is a broad term, and is to be given its ordinary and customary meaning to a person of ordinary skill in the art (and is not to be limited to a special or customized meaning), and refers without limitation to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members including one or more nitrogen, oxygen and sulfur in the ring backbone. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

As used herein, "heteroaralkyl" or "heteroarylalkyl" are broad terms, and are to be given their ordinary and customary meaning to a person of ordinary skill in the art (and are not to be limited to a special or customized meaning), and refer without limitation to a heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazolylalkyl, and imidazolylalkyl. In some cases, the alkylene group is a lower alkylene group (i.e., a $C_{1-4}$ alkylene group).

As used herein, "carbocyclyl" is a broad term, and is to be given its ordinary and customary meaning to a person of ordinary skill in the art (and is not to be limited to a special or customized meaning), and refers without limitation to a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

As used herein, "cycloalkyl" is a broad term, and is to be given its ordinary and customary meaning to a person of ordinary skill in the art (and is not to be limited to a special or customized meaning), and refers without limitation to a fully saturated carbocyclyl ring or ring system. Examples include cyclopropyl, cyclobutyl, cyclopentyl, and cyclohexyl.

As used herein, "cycloalkenyl" is a broad term, and is to be given its ordinary and customary meaning to a person of ordinary skill in the art (and is not to be limited to a special or customized meaning), and refers without limitation to a carbocyclyl ring or ring system having at least one double bond, wherein no ring in the ring system is aromatic. An example is cyclohexenyl.

As used herein, "heterocyclyl" is a broad term, and is to be given its ordinary and customary meaning to a person of ordinary skill in the art (and is not to be limited to a special or customized meaning), and refers without limitation to a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

As used herein, "acyl" is a broad term, and is to be given its ordinary and customary meaning to a person of ordinary skill in the art (and is not to be limited to a special or customized meaning), and refers without limitation to —C(=O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. Non-limiting examples include formyl, acetyl, propanoyl, benzoyl, and acryl.

As used herein, "O-carboxy" group is a broad term, and is to be given its ordinary and customary meaning to a person of ordinary skill in the art (and is not to be limited to a special or customized meaning), and refers without limitation to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

As used herein, "C-carboxy" group is a broad term, and is to be given its ordinary and customary meaning to a person of ordinary skill in the art (and is not to be limited to a special or customized meaning), and refers without limitation to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes carboxyl (i.e., —C(=O)OH).

As used herein, "cyano" group is a broad term, and is to be given its ordinary and customary meaning to a person of ordinary skill in the art (and is not to be limited to a special or customized meaning), and refers without limitation to a "—CN" group.

As used herein, "cyanato" group is a broad term, and is to be given its ordinary and customary meaning to a person of ordinary skill in the art (and is not to be limited to a special or customized meaning), and refers without limitation to an "—OCN" group.

As used herein, "isocyanato" group is a broad term, and is to be given its ordinary and customary meaning to a person of ordinary skill in the art (and is not to be limited to a special or customized meaning), and refers without limitation to a "—NCO" group.

As used herein, "thiocyanato" group is a broad term, and is to be given its ordinary and customary meaning to a person of ordinary skill in the art (and is not to be limited to a special or customized meaning), and refers without limitation to a "—SCN" group.

As used herein, "isothiocyanato" group is a broad term, and is to be given its ordinary and customary meaning to a person of ordinary skill in the art (and is not to be limited to a special or customized meaning), and refers without limitation to an "—NCS" group.

As used herein, "sulfinyl" group is a broad term, and is to be given its ordinary and customary meaning to a person of ordinary skill in the art (and is not to be limited to a special or customized meaning), and refers without limitation to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

As used herein, "sulfonyl" group is a broad term, and is to be given its ordinary and customary meaning to a person of ordinary skill in the art (and is not to be limited to a special or customized meaning), and refers without limitation to an "—SO₂R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

As used herein, "S-sulfonamido" group is a broad term, and is to be given its ordinary and customary meaning to a person of ordinary skill in the art (and is not to be limited to a special or customized meaning), and refers without limitation to a "—SO₂NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

As used herein, "N-sulfonamido" group is a broad term, and is to be given its ordinary and customary meaning to a person of ordinary skill in the art (and is not to be limited to a special or customized meaning), and refers without limitation to a "—N(R$^A$)SO₂R$_B$" group in which R$^A$ and R$_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

As used herein, "O-carbamyl" group is a broad term, and is to be given its ordinary and customary meaning to a person of ordinary skill in the art (and is not to be limited to a special or customized meaning), and refers without limitation to a "—OC(=O)NR$_A$R$_B$" group in which R$^A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

As used herein, "N-carbamyl" group is a broad term, and is to be given its ordinary and customary meaning to a person of ordinary skill in the art (and is not to be limited to a special or customized meaning), and refers without limitation to an "—N($R^A$)C(=O)O$R_B$" group in which $R^A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

As used herein, "O-thiocarbamyl" group is a broad term, and is to be given its ordinary and customary meaning to a person of ordinary skill in the art (and is not to be limited to a special or customized meaning), and refers without limitation to a "—OC(=S)N$R_A R_B$" group in which $R^A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

As used herein, "N-thiocarbamyl" group is a broad term, and is to be given its ordinary and customary meaning to a person of ordinary skill in the art (and is not to be limited to a special or customized meaning), and refers without limitation to an "—N($R^A$)C(=S)O$R_B$" group in which $R^A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

As used herein, "C-amido" group is a broad term, and is to be given its ordinary and customary meaning to a person of ordinary skill in the art (and is not to be limited to a special or customized meaning), and refers without limitation to a "—C(=O)N$R_A R_B$" group in which $R^A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

As used herein, "N-amido" group is a broad term, and is to be given its ordinary and customary meaning to a person of ordinary skill in the art (and is not to be limited to a special or customized meaning), and refers without limitation to a "—N($R^A$)C(=O)$R_B$" group in which $R^A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

As used herein, "amino" group is a broad term, and is to be given its ordinary and customary meaning to a person of ordinary skill in the art (and is not to be limited to a special or customized meaning), and refers without limitation to a "—N$R_A R^B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes free amino (i.e., —$NH_2$).

As used herein, "aminoalkyl" group is a broad term, and is to be given its ordinary and customary meaning to a person of ordinary skill in the art (and is not to be limited to a special or customized meaning), and refers without limitation to an amino group connected via an alkylene group.

As used herein, "alkoxyalkyl" group is a broad term, and is to be given its ordinary and customary meaning to a person of ordinary skill in the art (and is not to be limited to a special or customized meaning), and refers without limitation to an alkoxy group connected via an alkylene group, such as a "$C_{2-8}$ alkoxyalkyl" and the like. As used herein, "haloalkoxy" refers to the formula —OR wherein R is a haloalkyl as defined above, such as —$CF_3$, —$CHF_2$, —$CH_2F$, —$CH_2CF_3$, —$CH_2CHF_2$, —$CH_2CH_2F$, —$CH_2CH_2Cl$, or —$CH_2CF_2CF_3$.

As used herein, the term "substituted", as in a substituted group, is a broad term, and is to be given its ordinary and customary meaning to a person of ordinary skill in the art (and is not to be limited to a special or customized meaning), and refers without limitation to a group that is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_2$-$C_6$ alkenyl, $C_2$-$C_6$ alkynyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl(mercapto), halo($C_1$-$C_6$)alkyl (for example, —$CF_3$), halo($C_1$-$C_6$)alkoxy (for example, —$OCF_3$), $C_1$-$C_6$ alkylthio, arylthio, amino, amino($C_1$-$C_6$) alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O).

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene."

When two R groups are said to form a ring (for example, a heterocyclyl, or heteroaryl ring) "together with the atom to which they are attached," it is meant that the collective unit of the atom and the two R groups are the recited ring. The ring is not otherwise limited by the definition of each R group when taken individually.

Similarly, when two "adjacent" R groups are said to form a ring "together with the atoms to which they are attached," it is meant that the collective unit of the atoms, intervening bonds, and the two R groups are the recited ring. For example, when the following substructure is present:

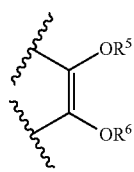

and $R^5$ and $R^6$ are defined as hydrogen or $R^A$, where adjacent $R^A$ together with the atoms to which they are attached form a heterocyclyl, or heteroaryl ring, it is meant that $R^5$ and $R^6$ can be selected from hydrogen or $R^A$, or alternatively, the substructure has structure:

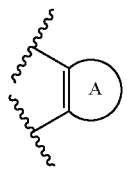

where A is a heterocyclyl, or heteroaryl ring containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a ⸺ substituent depicted as —AE— ⸺ includes the substituent being oriented such that the A is attached at the leftmost attachment point of the molecule as well as the case in which A is attached at the rightmost attachment point of the molecule.

The term "Subject" as used herein, is a broad term, and is to be given its ordinary and customary meaning to a person of ordinary skill in the art (and is not to be limited to a special or customized meaning), and refers without limitation to a human or a non-human mammal, for example, a dog, a cat, a mouse, a rat, a cow, a sheep, a pig, a goat, a non-human primate or a bird, for example, a chicken, as well as any other vertebrate or invertebrate.

The term "mammal" as used herein is a broad term, and is to be given its ordinary and customary meaning to a person of ordinary skill in the art (and is not to be limited to a special or customized meaning), and is used in its usual biological sense. Thus, it specifically includes, but is not limited to, primates, including simians (chimpanzees, apes, monkeys) and humans, cattle, horses, sheep, goats, swine, rabbits, dogs, cats, rodents, rats, mice guinea pigs, or the like.

An "effective amount" or a "therapeutically effective amount" are broad terms, and are to be given their ordinary and customary meaning to a person of ordinary skill in the art (and are not to be limited to a special or customized meaning), and refer without limitation to an amount of a therapeutic agent that is effective to relieve, to some extent, or to reduce the likelihood of onset of, one or more of the symptoms of a disease or condition, and includes curing a disease or condition. "Curing" means that the symptoms of a disease or condition are eliminated; however, certain long-term or permanent effects may exist even after a cure is obtained (such as extensive tissue damage).

"Treat," "treatment," or "treating," as used herein are broad terms, and are to be given their ordinary and customary meaning to a person of ordinary skill in the art (and are not to be limited to a special or customized meaning), and refer without limitation to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

Administration and Pharmaceutical Compositions

Administration of any compounds or pharmaceutically active substances disclosed herein or any pharmaceutically acceptable salts thereof can be administered via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly.

The compounds useful as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated herein by reference in its entirety. Accordingly, some embodiments include pharmaceutical compositions comprising: (a) a safe and therapeutically effective amount of a compound described herein (including enantiomers, diastereoisomers, tautomers, polymorphs, and solvates thereof), or pharmaceutically acceptable salts thereof; and (b) a pharmaceutically acceptable carrier, diluent, excipient or combination thereof.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, for example, in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (for example, from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions include compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modem Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carriers suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort may be maximized as much as possible, although sometimes formulation considerations (for example drug stability) may necessitate less than optimal comfort. In the case that comfort cannot be maximized, the liquid may be formulated such that the liquid is tolerable to the patient for topical ophthalmic use. Additionally, an ophthalmically acceptable liquid may either be packaged for single use, or contain a preservative to prevent contamination over multiple uses.

For ophthalmic application, solutions or medicaments are often prepared using a physiological saline solution as a major vehicle. Ophthalmic solutions may preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan. In some embodiments, a daily dose may be from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. Thus, for administration to a 70 kg person, the dosage range would be from about 17 mg per day to about 8000 mg per day, from about 35 mg per day or less to about 7000 mg per day or more, from about 70 mg per day to about 6000 mg per day, from about 100 mg per day to about 5000 mg per day, or from about 200 mg to about 3000 mg per day.

Methods of Treatment

Some embodiments include methods of treating an aneurysm with and compositions comprising compounds described herein. Some methods include administering a compound, composition, pharmaceutical composition described herein to a subject in need thereof. In some embodiments, a subject can be an animal, for example, a mammal, a human. In some embodiments, the subject is a human.

Further embodiments include administering a combination of compounds to a subject in need thereof. A combination can include a compound, composition, pharmaceutical composition described herein with an additional medicament.

Some embodiments include co-administering a compound, composition, and/or pharmaceutical composition described herein, with an additional medicament. By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment the agents are administered through the same route, such as orally. In another embodiment, the agents are administered through different routes, such as one being administered orally and another being administered intravenously.

Examples of additional medicaments include collagen crosslinking agents, such as glutaraldehyde, genipin acyl azide, and/or epoxyamine.

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

Although the invention has been described with reference to embodiments and examples, it should be understood that numerous and various modifications can be made without departing from the spirit of the invention. Accordingly, the invention is limited only by the following claims.

It is understood that this disclosure, in many respects, is only illustrative of the numerous alternative device embodiments. Changes may be made in the details, particularly in matters of shape, size, material and arrangement of various device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention. In addition, while certain features and elements have been described in connection with particular embodiments, those skilled in the art will appreciate that those features and elements can be combined with the other embodiments disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (for example, compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (for example, where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description

What is claimed is:

1. A method for treating an aneurysm in a blood vessel of a patient, the method comprising:
    positioning a first balloon upstream of the aneurysm;
    positioning a conformable second balloon adjacent the aneurysm, wherein an expandable membrane of the conformable second balloon is sufficiently compliant to expand entirely into a sealed space within the aneurysm such that an outer surface of the conformable second balloon conforms to a shape of the sealed space within the aneurysm;
    inflating the first balloon to occlude a downstream blood flow;
    after the inflating of the first balloon, expanding the conformable second balloon to occlude a retrograde blood flow and displace blood from the aneurysm; and
    after the expanding of the conformable second balloon, delivering a therapeutic agent to the aneurysm through pores in the conformable second balloon,
    wherein the the pores of the conformable second balloon are configured to place an interior volume of the conformable second balloon in fluid communication with an intravascular environment of the aneurysm.

2. The method of claim 1, wherein the expanding of the conformable second balloon comprises introducing an inflation fluid into the interior volume of the conformable second balloon.

3. The method of claim 1, wherein the delivering of the therapeutic agent comprises introducing a solution comprising the therapeutic agent into the interior volume of the conformable second balloon, the introduction of the solution being configured to expand and/or maintain an expanded state of the conformable second balloon.

4. The method of claim 1, wherein the inflating of the first balloon and the expanding of the conformable second balloon creates a sealed volume within the blood vessel between the first balloon and the conformable second balloon.

5. The method of claim 4, wherein the delivering of the therapeutic agent comprises introducing the therapeutic agent into the sealed volume.

6. The method of claim 5, wherein the therapeutic agent is not delivered into the blood vessel outside of the sealed volume while the sealed volume is established.

7. The method of claim 1, wherein the inflating of, the first balloon anchors the first balloon and the conformable second balloon within the blood vessel.

8. The method of claim 1, wherein the positioning of the conformable second balloon adjacent the aneurysm comprises the positioning of the conformable second balloon across the aneurysm.

9. The method of claim 1, wherein the positioning of the conformable second balloon adjacent the aneurysm comprises the positioning of the conformable second balloon along a downstream edge of the aneurysm and wherein the expanding of the conformable second balloon creates a sealed volume between the first balloon and the conformable second balloon which encompasses the aneurysm.

10. The method of claim 1, wherein the positioning of the conformable second balloon adjacent the aneurysm comprises the positioning of the conformable second balloon such that a length of the aneurysm along the blood vessel encompasses an entire length of the conformable second balloon.

11. The method of claim 1, further comprising maintaining the conformable second balloon in an expanded state by maintaining a pressure within the interior volume of the conformable second balloon greater than a diastolic blood pressure of the patient and les than a systolic blood pressure of the patient.

12. The method of claim 1, wherein the expanding of the conformable second balloon and the delivering of the therapeutic agent to the aneurysm through the pores comprises introducing a solution into the interior volume of the conformable second balloon, and wherein the solution is introduced at a first volumetric flow rate to expand the conformable second balloon and the solution is introduced at a second volumetric flow rate to deliver the therapeutic agent through the pores, the first volumetric flow rate being greater than or equal to the second volumetric flow rate.

13. The method of claim 12, wherein the first volumetric flow rate is greater than the second volumetric flow rate.

14. The method of claim 1, wherein a blood flow is occluded within the blood vessel for no longer than approximately 3 minutes.

15. The method of claim 14, wherein at least 1 mL of a solution N comprising the therapeutic agent is delivered while the downstream blood flow and the retrograde blood flow of the blood vessel is occluded.

16. The method of claim 1, wherein the therapeutic agent comprises pentagalloyl glucose (PGG).

17. A method for treating an aneurysm in a blood vessel of a patient, the method comprising:
    positioning a first balloon upstream of the aneurysm;
    positioning a second balloon adjacent the aneurysm, wherein an expandable membrane of the second balloon is sufficiently compliant to expand entirely into a sealed space within the aneurysm such that an outer surface of the second balloon conforms to a shape of the sealed space within the aneurysm;
    inflating the first balloon to occlude a downstream blood flow;
    after the inflating of the first balloon, expanding the second balloon to occlude a retrograde blood flow and to cause the outer surface of the second balloon to conform to the shape of the sealed space within the aneurysm; and delivering a therapeutic agent to the aneurysm through pores in the second baloon.

18. The method of claim 17, wherein the inflating of the first balloon and the expanding of the second balloon creates a sealed volume within the blood vessel between the first balloon and the second balloon.

19. The method of claim 17, wherein the expanding of the second balloon comprises the expanding of the second balloon to a greater expanded diameter than an inflated diameter of the first balloon.

20. The method of claim 17:
wherein the inflating of the first balloon comprises the inflating of the first balloon to an inflation pressure greater than or equal to a systolic blood pressure of the patient and maintaining the inflation pressure;
wherein the expanding of the second balloon comprises the expanding of the second balloon to a pressure greater than or equal to a diastolic blood pressure of the patient and maintaining the pressure.

\* \* \* \* \*

UNITED STATES PATENT AND TRADEMARK OFFICE
CERTIFICATE OF CORRECTION

| | | |
|---|---|---|
| PATENT NO. | : 12,144,506 B2 | Page 1 of 2 |
| APPLICATION NO. | : 18/190692 | |
| DATED | : November 19, 2024 | |
| INVENTOR(S) | : Eric Wells et al. | |

It is certified that error appears in the above-identified patent and that said Letters Patent is hereby corrected as shown below:

On the Title Page

In Column 2, Line 14, Item (57) under Abstract, delete "sealed volume The" and insert --sealed volume. The--.

In the Specification

In Column 3, Line 10, delete "$R^7$, $R^5$, $R^9$," and insert --$R^7$, $R^8$, $R^9$,--.

In Column 3, Line 60, delete "—N(R)$_2$," and insert -- —N($R^Y$)$_2$,--.

In Column 3, Line 61, delete "N(R)$_2$," and insert --N($R^Y$)$_2$,--.

In Column 3, Line 62, delete "N(R)$_2$," and insert --N($R^Y$)$_2$,--.

In Column 4, Line 13, delete "$R^6$, $R^1$, $R^1$, $R^9$," and insert --$R^6$, $R^7$, $R^8$, $R^9$,--.

In Column 42, Line 58, delete ""—N($R^A$)SO$_2$R$_B$"" and insert --"—N(R$_A$)SO$_2$R$_B$"--.

In Column 42, Line 58, delete "which $R^A$" and insert --which R$_A$--.

In Column 42, Line 67, delete "which $R^A$" and insert --which R$_A$--.

In Column 43, Line 9, delete ""—N($R^A$)C" and insert --"—N(R$_A$)C--.

In Column 43, Line 9, delete "which $R^A$ and" and insert --which R$_A$ and--.

In Column 43, Line 18, delete "which $R^A$ and" and insert --which R$_A$ and--.

Signed and Sealed this
Eleventh Day of March, 2025

Coke Morgan Stewart
*Acting Director of the United States Patent and Trademark Office*

CERTIFICATE OF CORRECTION (continued)
U.S. Pat. No. 12,144,506 B2

In Column 43, Line 27, delete ""—N(R$^A$)C" and insert --"—N(R$_A$)C--.

In Column 43, Line 27, delete "which R$^A$ and" and insert --which R$_A$ and--.

In Column 43, Line 36, delete "which R$^A$ and" and insert --which R$_A$ and--.

In Column 43, Line 45, delete ""—N(R$^A$)C" and insert --"—N(R$_A$)C--.

In Column 43, Line 45, delete "which R$^A$ and" and insert --which R$_A$ and--.

In Column 43, Line 54, delete ""—NR$_A$R$^B$" group" and insert --"—NR$_A$R$_B$" group--.

In Column 45, Line 31 (Approx.), delete "a [figure]" and insert --a--.

In Column 45, Lines 31-32 (Approx.), delete "[figure]" and insert --[figure]--.

In the Claims

In Column 53, Claim 1, Line 49, delete "wherein the the pores" and insert --wherein the pores--.

In Column 54, Claim 7, Line 7, delete "inflating of, the" and insert --inflating of the--.

In Column 54, Claim 11, Line 32, delete "and les than" and insert --and less than--.

In Column 54, Claim 15, Line 50, delete "solution N comprising the" and insert --solution comprising--.

In Column 55, Claim 17, Line 5, delete "baloon." and insert --balloon.--.

In Column 55, Claim 20, Line 18, delete "pressure;" and insert --pressure; and--.